(12) United States Patent
Song et al.

(10) Patent No.: US 11,248,210 B2
(45) Date of Patent: Feb. 15, 2022

(54) METHOD FOR ISOLATION OF STEM CELLS FROM BONE MARROW USING SUBFRACTIONATION CULTURING METHOD AND PROLIFERATION THEREOF

(71) Applicant: SCM LIFESCIENCE CO., LTD., Incheon (KR)

(72) Inventors: Sun Uk Song, Incheon (KR); Si Na Kim, Incheon (KR); Yun Kyoung Cho, Incheon (KR); Dong Sik Ham, Incheon (KR)

(73) Assignee: SCM LIFESCIENCE CO., LTD., Incheon (KR)

( * ) Notice: Subject to any disclaimer, the term of this patent is extended or adjusted under 35 U.S.C. 154(b) by 172 days.

(21) Appl. No.: 16/026,497

(22) Filed: Jul. 3, 2018

(65) Prior Publication Data

US 2019/0136189 A1 May 9, 2019

(30) Foreign Application Priority Data

Nov. 6, 2017 (KR) .................. 10-2017-0146906

(51) Int. Cl.
*C12N 5/0775* (2010.01)
*C12N 5/077* (2010.01)
*A61K 35/28* (2015.01)
*C12N 5/0789* (2010.01)

(52) U.S. Cl.
CPC ............ *C12N 5/0654* (2013.01); *A61K 35/28* (2013.01); *C12N 5/0647* (2013.01); *C12N 5/0663* (2013.01); *C12N 5/0662* (2013.01); *C12N 2500/30* (2013.01); *C12N 2500/70* (2013.01); *C12N 2501/00* (2013.01); *C12N 2506/1353* (2013.01); *C12N 2513/00* (2013.01); *C12N 2523/00* (2013.01)

(58) Field of Classification Search
CPC .. C12N 5/0654; C12N 5/0647; C12N 5/0663; C12N 2506/1353; C12N 5/0662; C12N 5/0607

See application file for complete search history.

(56) References Cited

U.S. PATENT DOCUMENTS

| 2008/0299656 A1* | 12/2008 | Song | C12N 5/0607 435/383 |
| 2013/0005036 A1* | 1/2013 | Song | C12N 5/0607 435/374 |

OTHER PUBLICATIONS

Yi et al., Manufacture of clinical-grade human clonal mesenchymal stem cell products from single colony forming-unit derived colonies based on the subfractionation culturing method. Tissue Engineering Part C:Methods, vol. 21, No. 12 (Nov. 5, 2015) pp. 1251-1262. (Year: 2015).*
Choi et al., Effect of ascorbic acid on bone marrow-derived mesenchymal stem cell proliferation and differentiation. Journal of Bioscience and Bioengineering, vol. 105, No. 6 (Jun. 2008) pp. 586-594. (Year: 2008).*
R. Ian Freshney, "Defined Media and Supplements." In: Culture of Animal Cell: A Manual of Basic Technique and Specialized Applications. (Hoboken, NJ, John Wiley & Sons, Inc., 2010), pp. 99-114. QH585.2.F74 2010. (Year: 2010).*
Jeon et al., Characterization of mouse clonal mesenchymal stem cell lines established by subfractionation culturing method. World Journal of Stem Cells, vol. 3, No. 8 (Aug. 26, 2011) pp. 70-82. (Year: 2011).*
R. Ian Freshney, Culture of Animal Cell: A Manual of Basic Technique and Specialized Applications. (Hoboken, NJ, John Wiley & Sons, Inc., 2010), Chps. 8, 20, and 22. QH585.2.F74 2010. (Year: 2010).*
Yi et al., Isolation of adipose-derived stem cells by using a subfractionation culturing method. Expert Opinion on Biological Therapy, vol. 14, No. 11 (2014) pp. 1551-1560. (Year: 2014).*

* cited by examiner

*Primary Examiner* — Kara D Johnson
(74) *Attorney, Agent, or Firm* — Sughrue Mion, PLLC

(57) ABSTRACT

The present disclosure relates to a subfractionation culturing method of a stem cell and proliferation method of a monoclonal stem cell obtained using the same. According to the subfractionation culturing method of stem cells and the proliferation thereof of the exemplary embodiments of the present disclosure, it is advantage that monoclonal stem cells may be quickly obtained without contamination, and desired monoclonal stem cells may be largely obtained in a short time through the rapid proliferation, thereby being used for the preparation of stem cell-therapeutic agents.

8 Claims, 26 Drawing Sheets

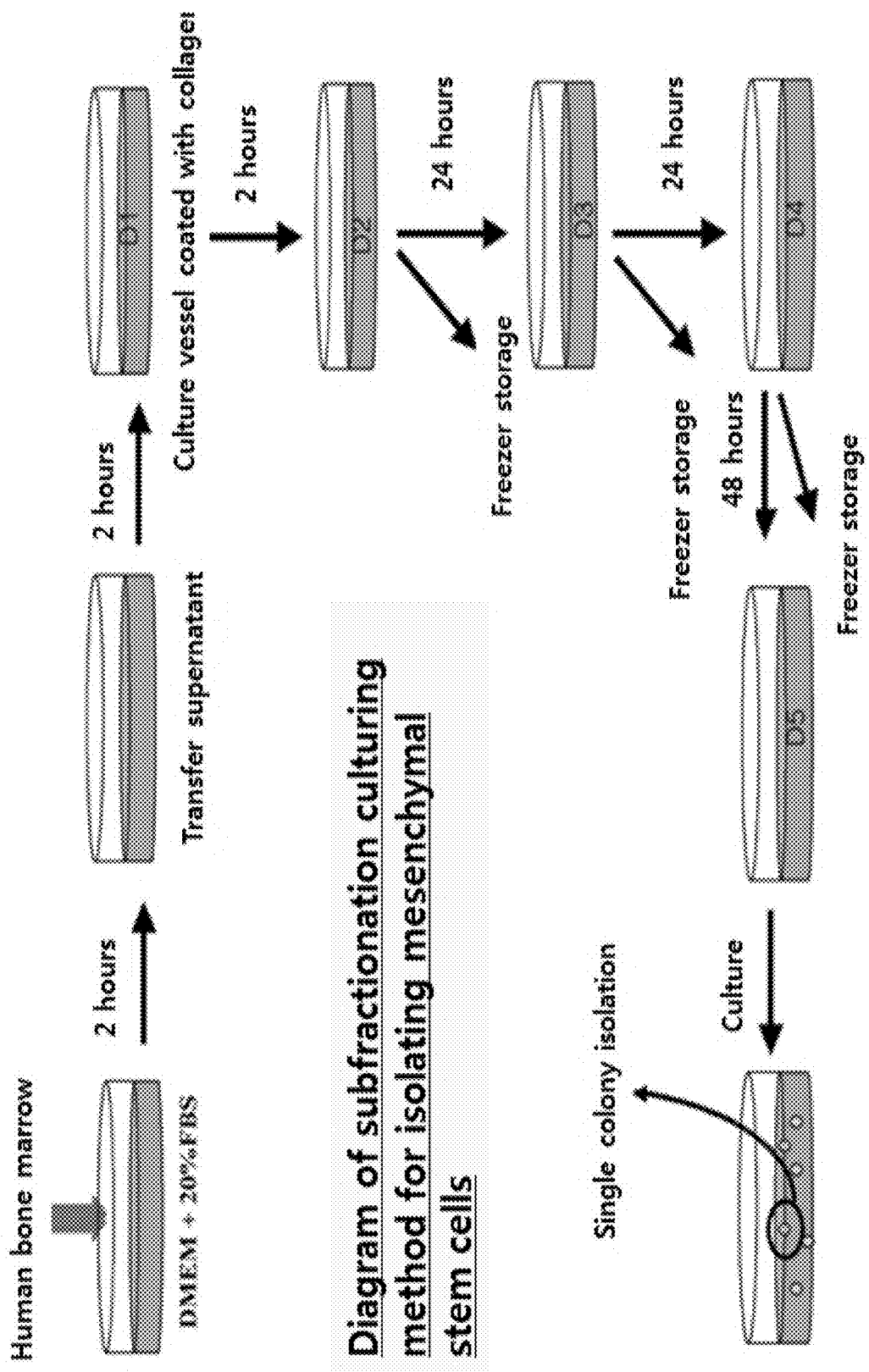
[FIG. 1]

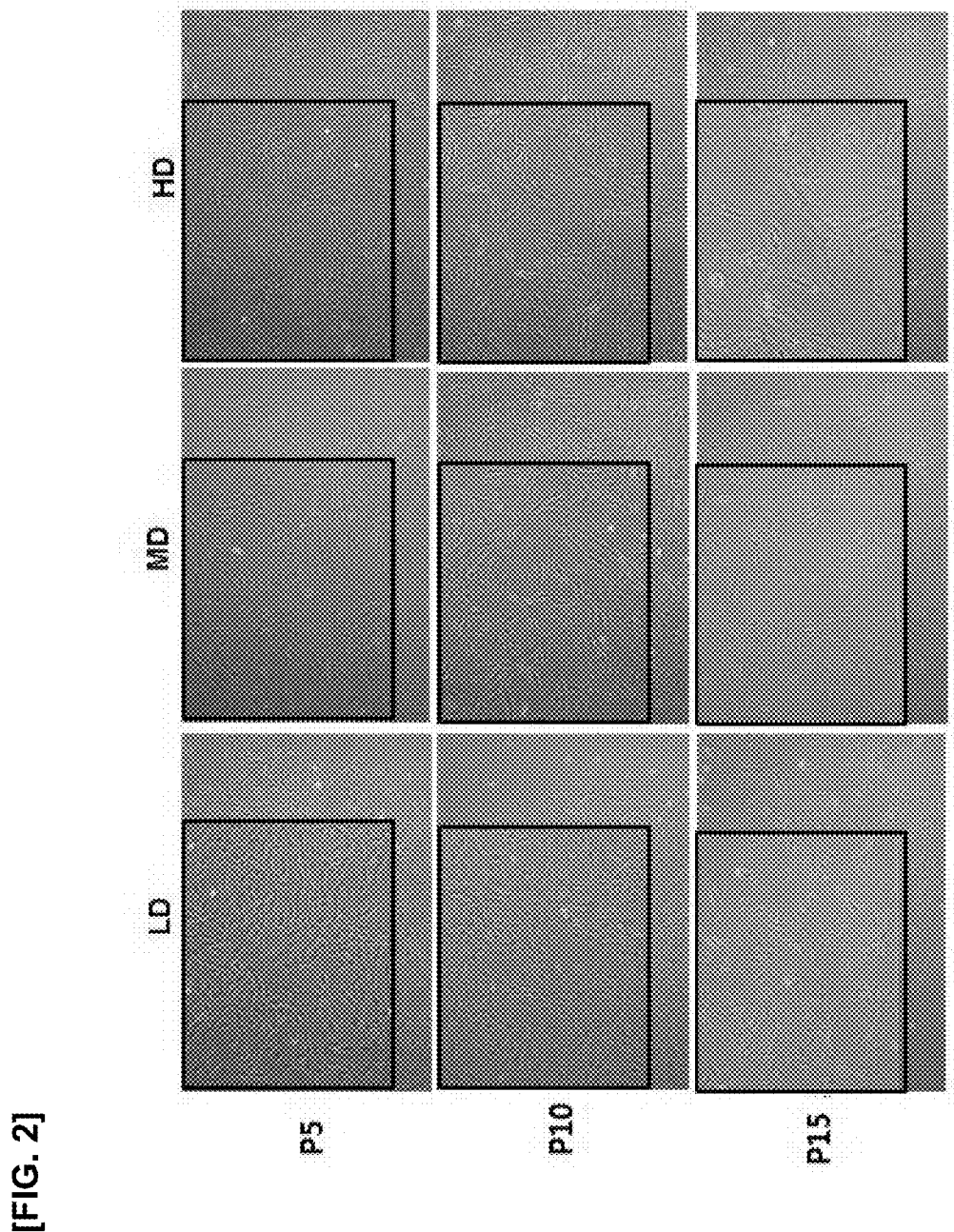
[FIG. 2]

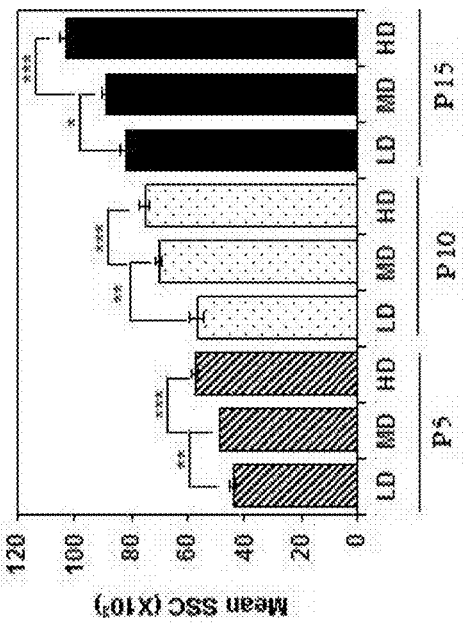
[FIG. 3A]
[FIG. 3B]
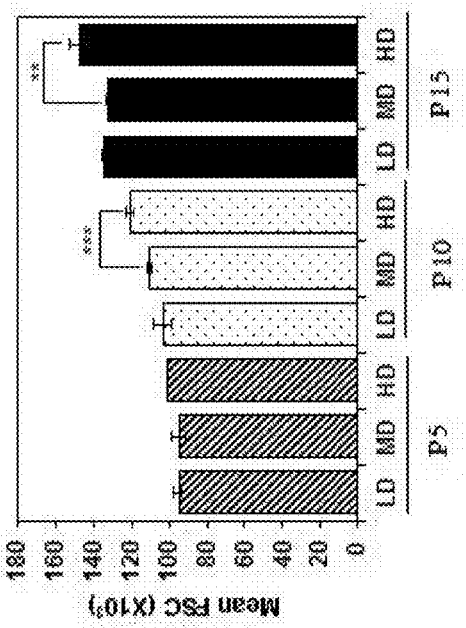
[FIG. 3]

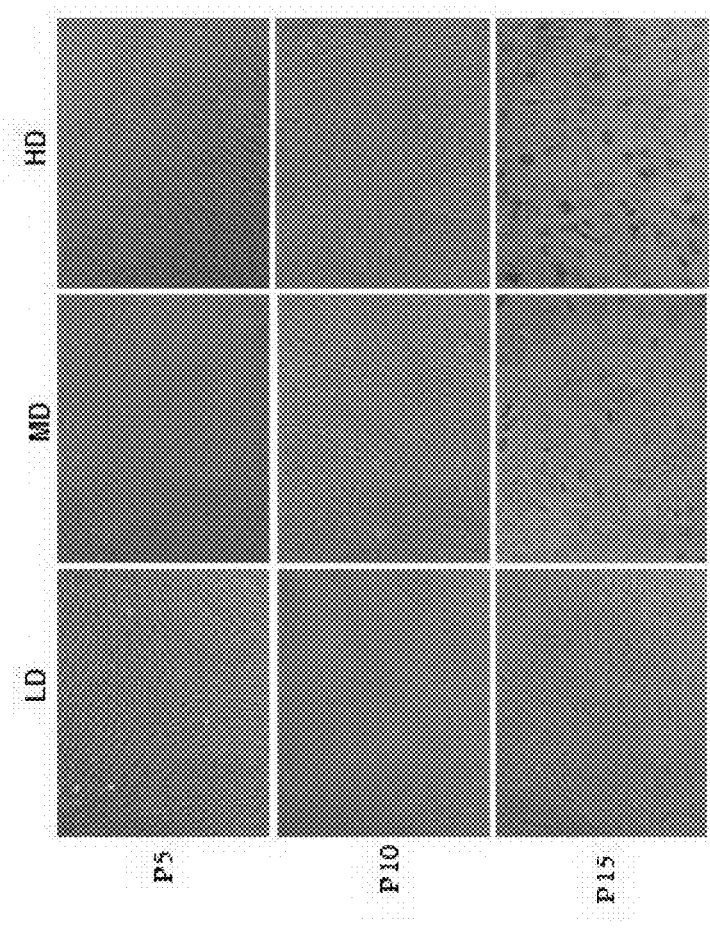
[FIG. 4]

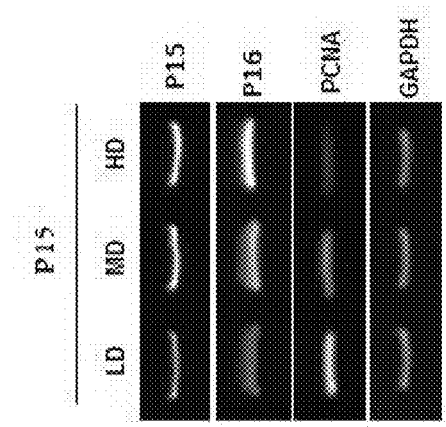
[FIG. 5]

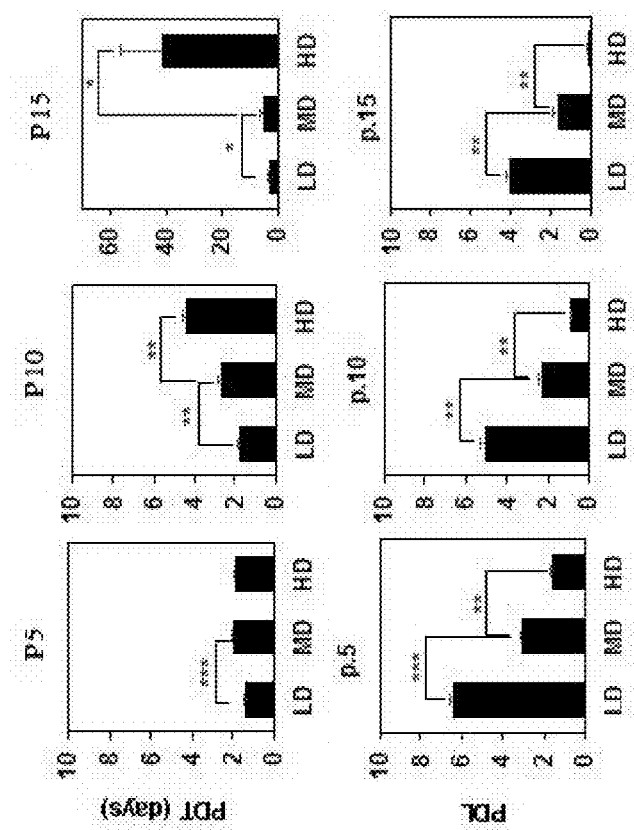
[FIG. 6]

[FIG. 7A]
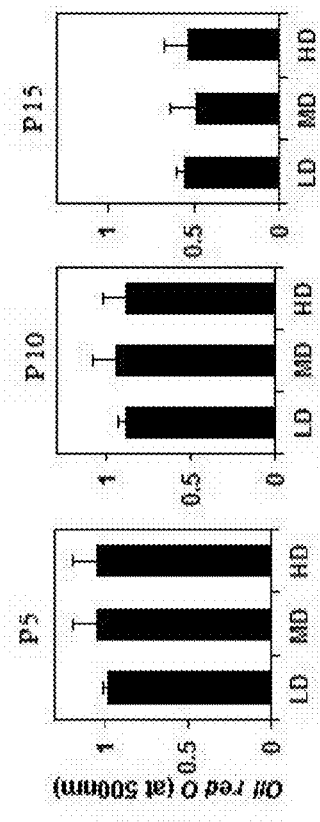
[FIG. 7B]
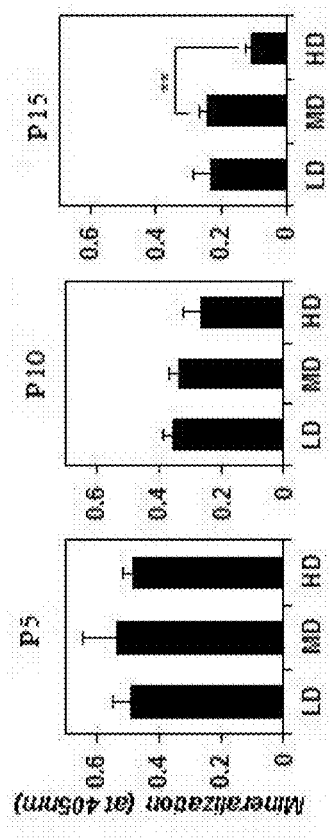
[FIG. 7C]
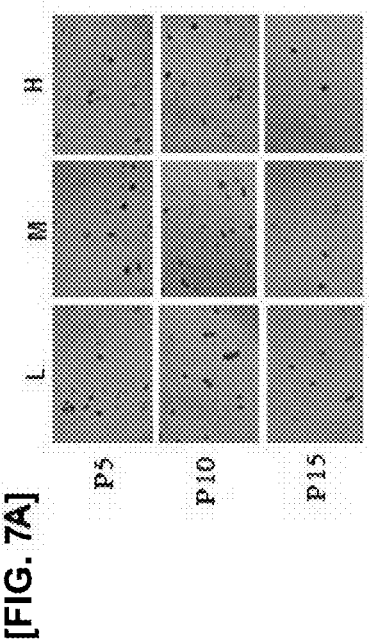
[FIG. 7D]
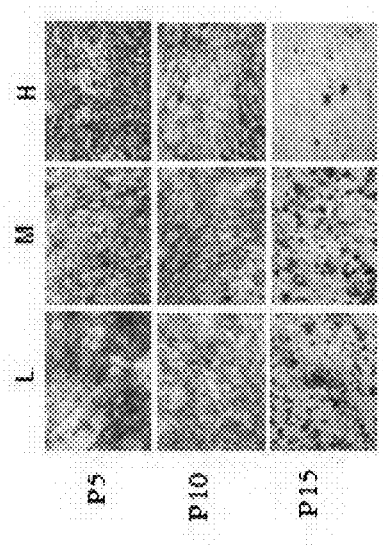
[FIG. 7]

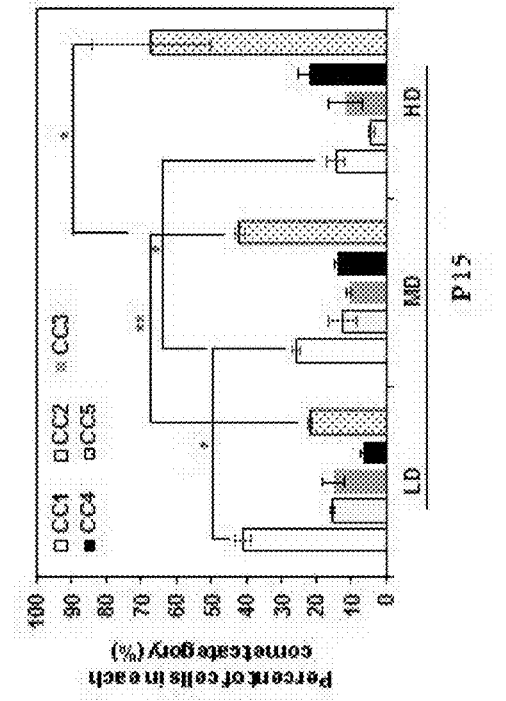
[FIG. 8B]
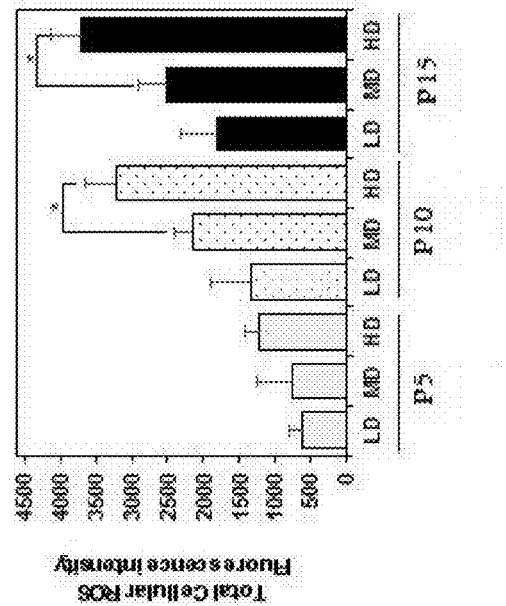
[FIG. 8A]
[FIG. 8]

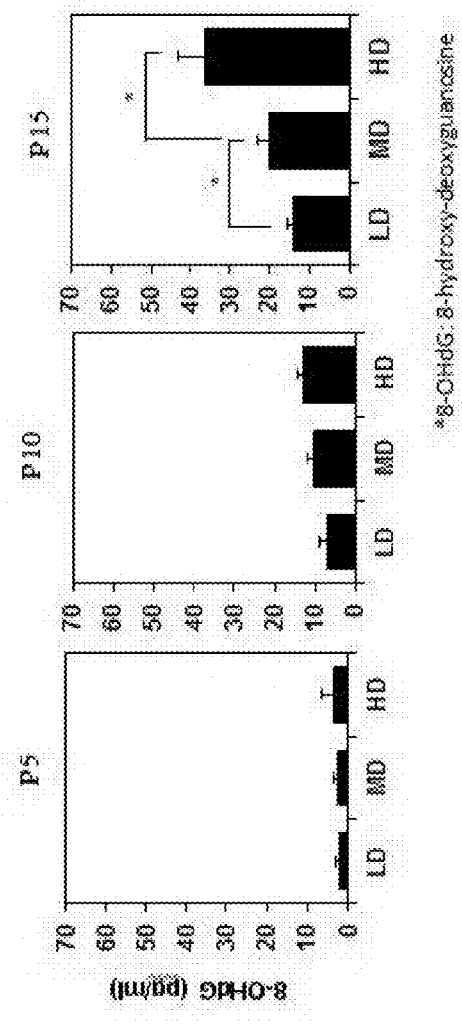
[FIG. 9]

[FIG. 10]

| Fold Increase (F.I) | | | |
|---|---|---|---|
| cell/cm² | P11 | P13 | P15 |
| HD | 2.6±0.3 | 1.9±0.2 | 1.6±0.1 |
| HD + AA | 3.8±0.5 | 2.9±0.1 | 2.5±0.2 |

| Relative Proliferation Index | | | |
|---|---|---|---|
| cell/cm² | p11 | p13 | p15 |
| HD | 1 | 1 | 1 |
| HD + AA | 1.46 | 1.52 | 1.56 |

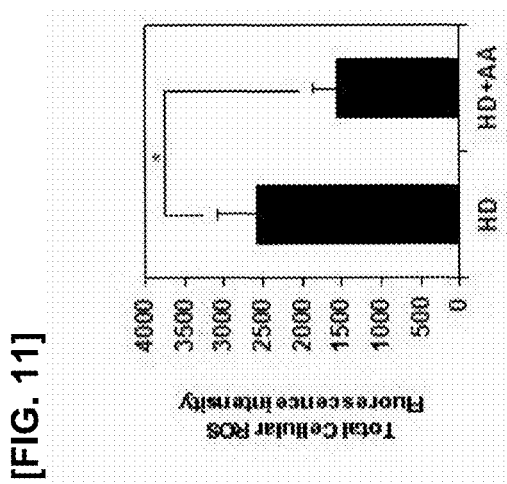
[FIG. 11]

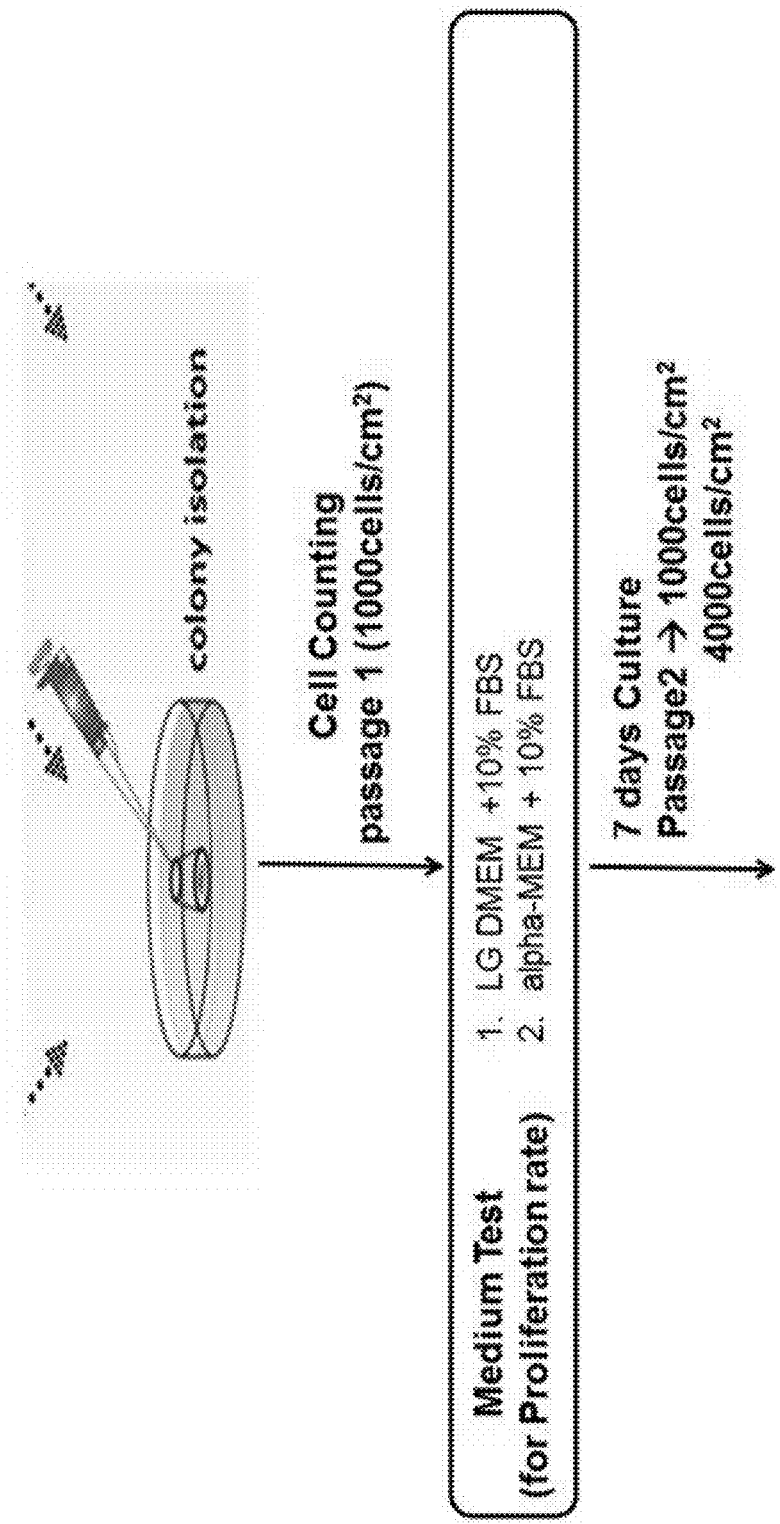
[FIG. 12]

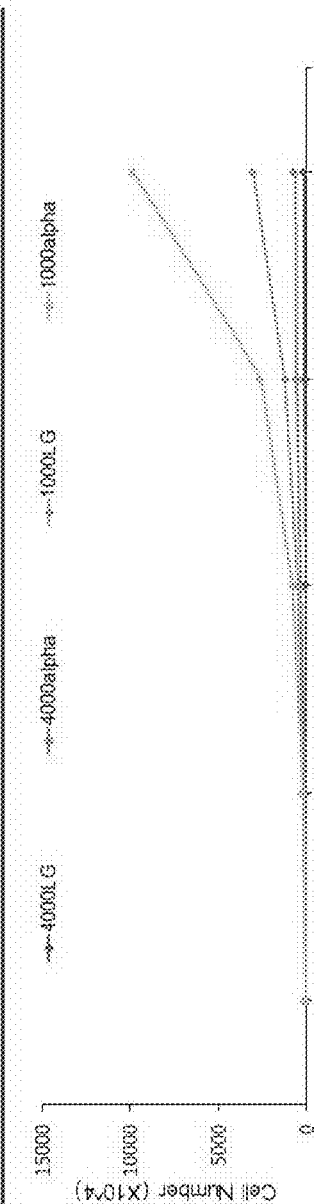
[FIG. 13A]
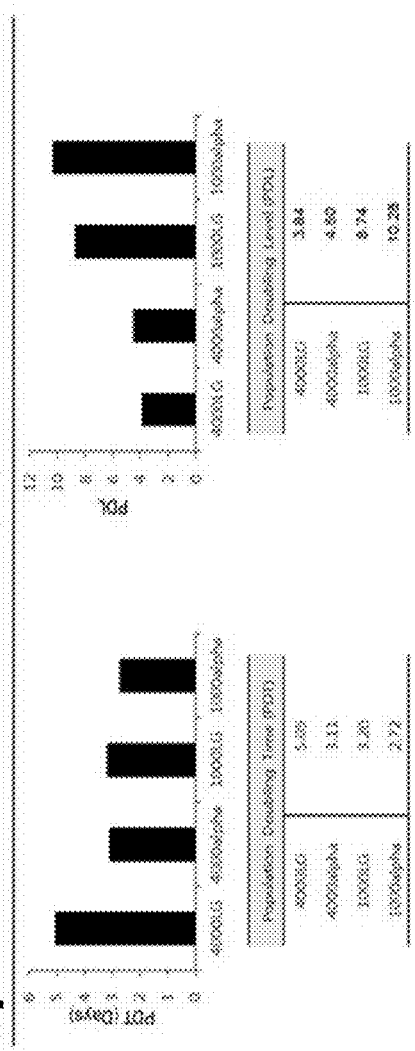
[FIG. 13B]
[FIG. 13]

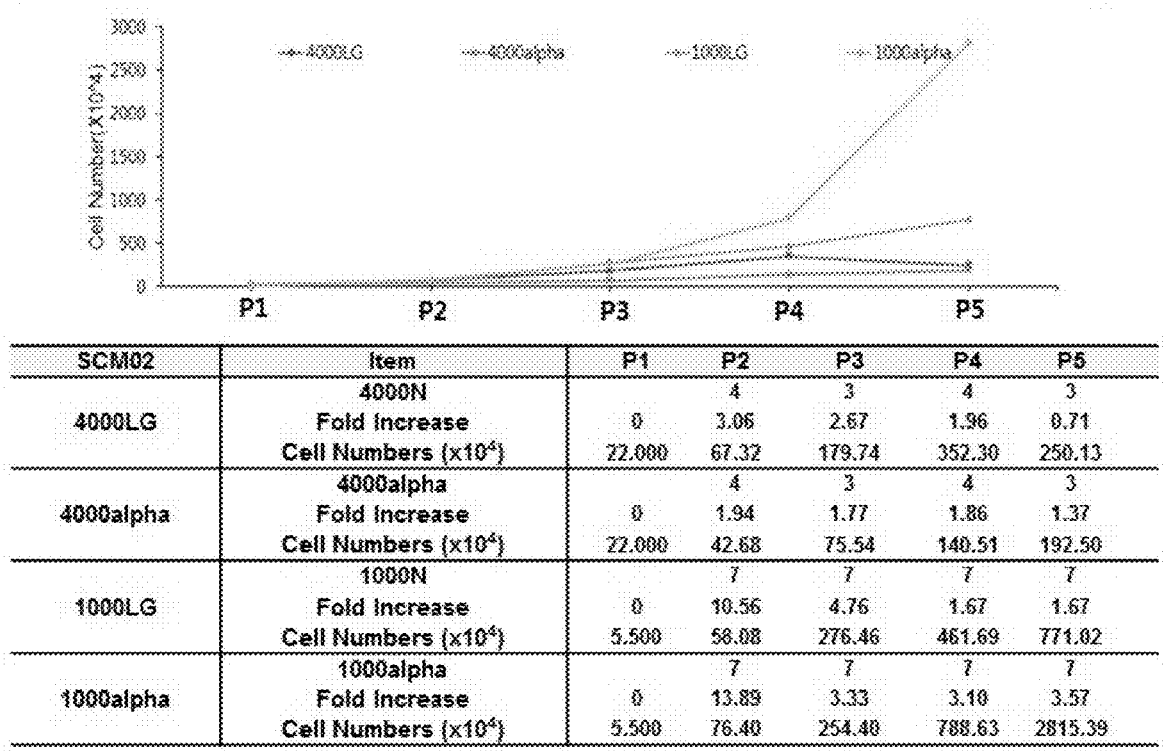
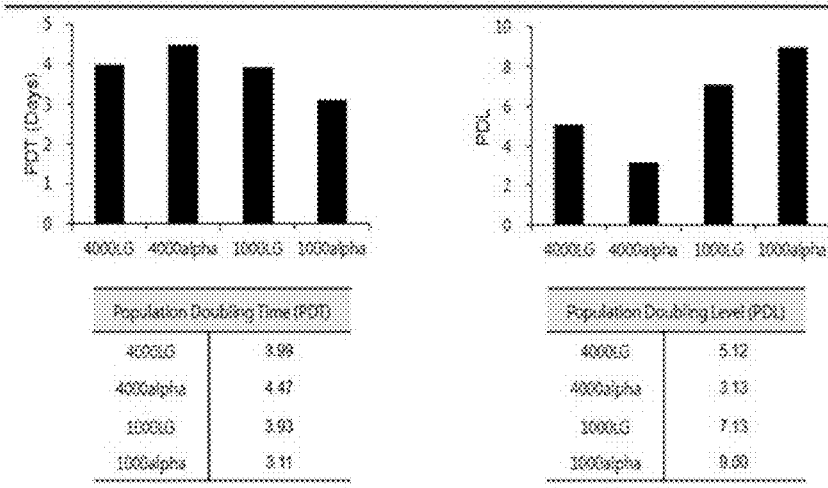
[FIG. 14]

[FIG. 15A]
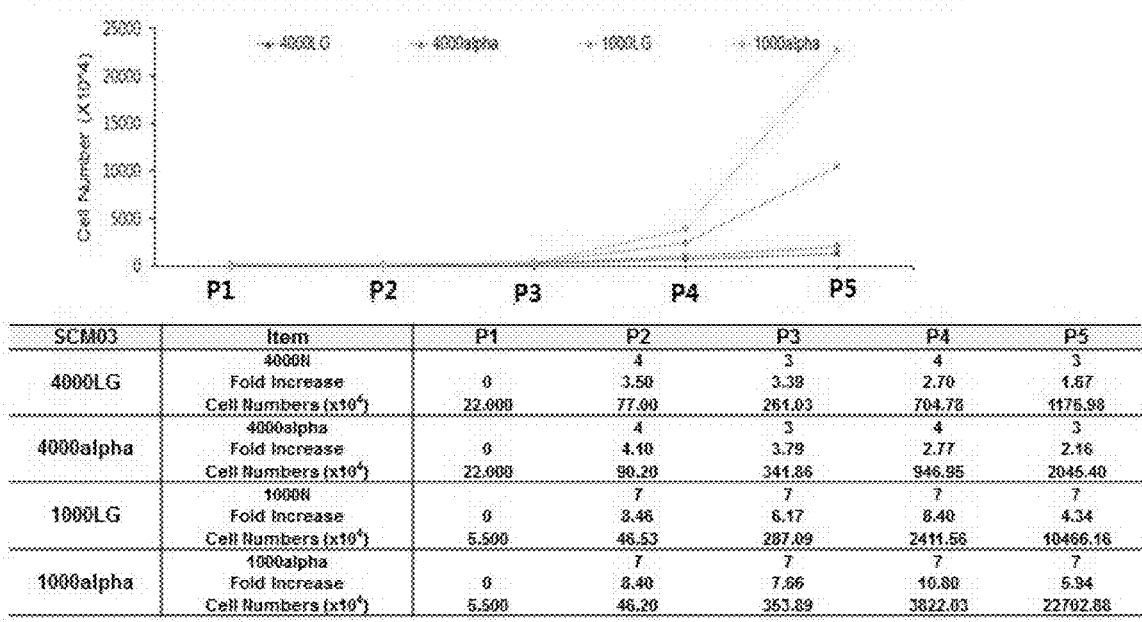
[FIG. 15B]
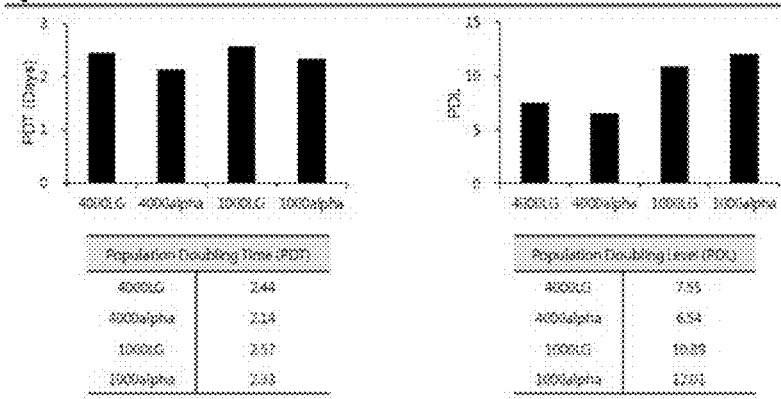
[FIG. 15]

[FIG. 16A] SCM04
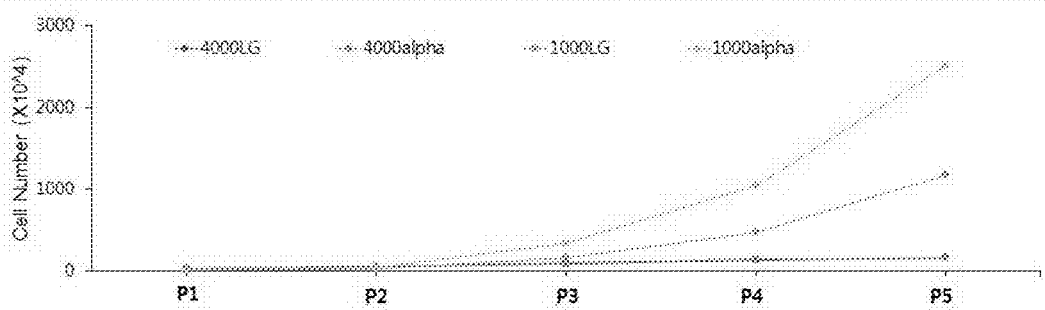
| SCM04 | Item | P1 | P2 | P3 | P4 | P5 |
|---|---|---|---|---|---|---|
| 4000LG | 4000N | | 4 | 3 | 4 | 3 |
| | Fold Increase | 0 | 2.57 | 1.57 | 1.51 | 1.16 |
| | Cell Numbers (x10⁴) | 22.000 | 56.54 | 88.77 | 134.04 | 155.49 |
| 4000alpha | 4000alpha | | 4 | 3 | 4 | 3 |
| | Fold Increase | 0 | 2.70 | 1.82 | 1.33 | 1.14 |
| | Cell Numbers (x10⁴) | 22.000 | 59.40 | 108.11 | 143.78 | 163.91 |
| 1000LG | 1000N | | 7 | 7 | 7 | 7 |
| | Fold Increase | 0 | 6.29 | 4.80 | 2.86 | 2.49 |
| | Cell Numbers (x10³) | 5.500 | 34.60 | 166.06 | 474.92 | 1182.55 |
| 1000alpha | 1000alpha | | 7 | 7 | 7 | 7 |
| | Fold Increase | 0 | 9.00 | 6.68 | 3.17 | 2.40 |
| | Cell Numbers (x10⁴) | 5.500 | 49.50 | 331.16 | 1049.76 | 2519.43 |
[FIG. 16B] SCM04
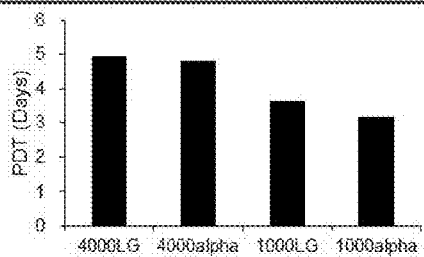
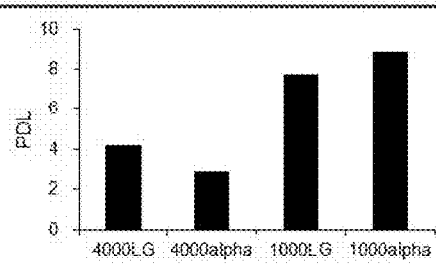
| Population Doubling Time (PDT) | |
|---|---|
| 4000LG | 4.96 |
| 4000alpha | 4.83 |
| 1000LG | 3.61 |
| 1000alpha | 3.17 |
| Population Doubling Level (PDL) | |
|---|---|
| 4000LG | 4.18 |
| 4000alpha | 2.90 |
| 1000LG | 7.75 |
| 1000alpha | 8.84 |
[FIG. 16]

[FIG. 17A]
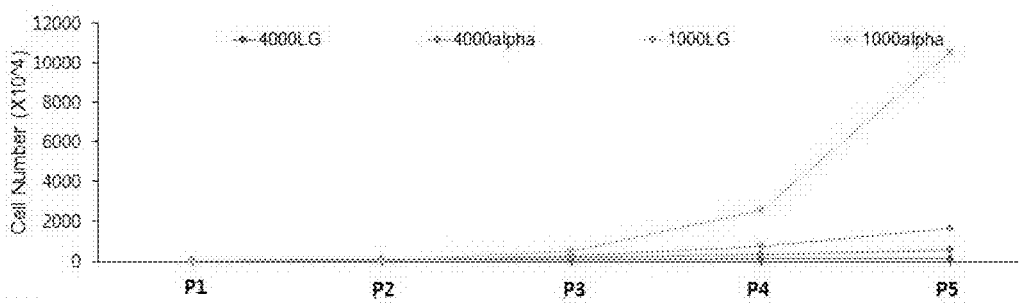
| SCM05 | Item | P1 | P2 | P3 | P4 | P5 |
|---|---|---|---|---|---|---|
| 4000LG | 4000N | | 4 | 3 | 4 | 3 |
| | Fold Increase | 0 | 3.27 | 1.49 | 1.19 | 1.13 |
| | Cell Numbers (x10$^4$) | 22.000 | 71.94 | 107.19 | 127.56 | 144.14 |
| 4000alpha | 4000alpha | | 4 | 3 | 4 | 3 |
| | Fold Increase | 0 | 4.64 | 2.14 | 1.67 | 1.63 |
| | Cell Numbers (x10$^4$) | 22.000 | 102.08 | 218.45 | 364.81 | 594.65 |
| 1000LG | 1000N | | 7 | 7 | 7 | 7 |
| | Fold Increase | 0 | 8.57 | 5.71 | 2.66 | 2.14 |
| | Cell Numbers (x10$^4$) | 5.500 | 47.14 | 269.14 | 769.74 | 1647.25 |
| 1000alpha | 1000alpha | | 7 | 7 | 7 | 7 |
| | Fold Increase | 0 | 10.95 | 8.24 | 5.24 | 4.05 |
| | Cell Numbers (x10$^4$) | 5.500 | 60.23 | 496.25 | 2600.37 | 10531.50 |
[FIG. 17B]     SCM05
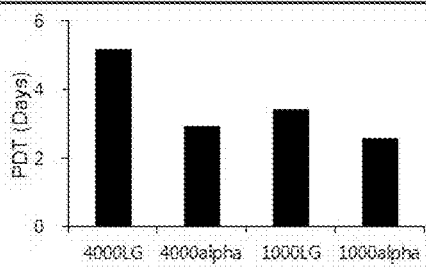
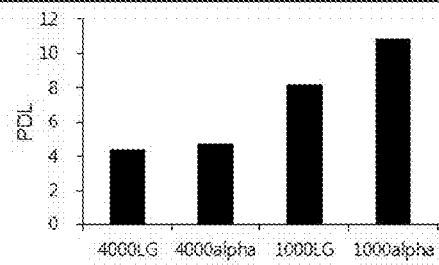
| Population Doubling Time (PDT) | |
|---|---|
| 4000LG | 5.16 |
| 4000alpha | 2.94 |
| 1000LG | 3.40 |
| 1000alpha | 2.57 |
| Population Doubling Level (PDL) | |
|---|---|
| 4000LG | 4.42 |
| 4000alpha | 4.76 |
| 1000LG | 8.23 |
| 1000alpha | 10.90 |
[FIG. 17]

[FIG 18A]
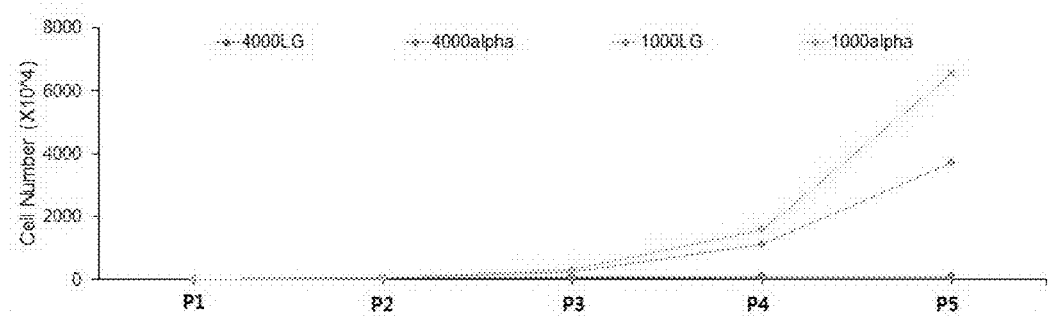
[FIG. 18B]
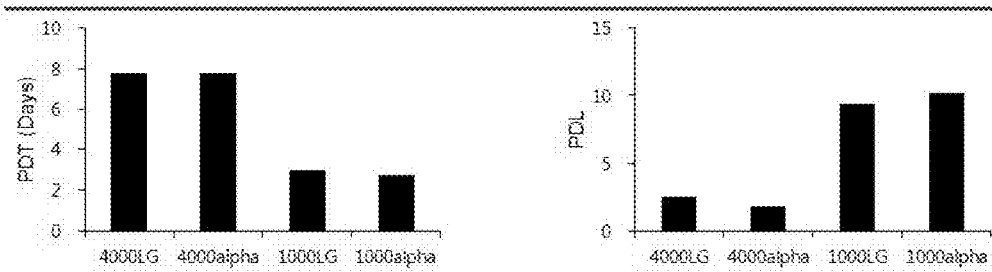
[FIG. 18]

[FIG. 19A]
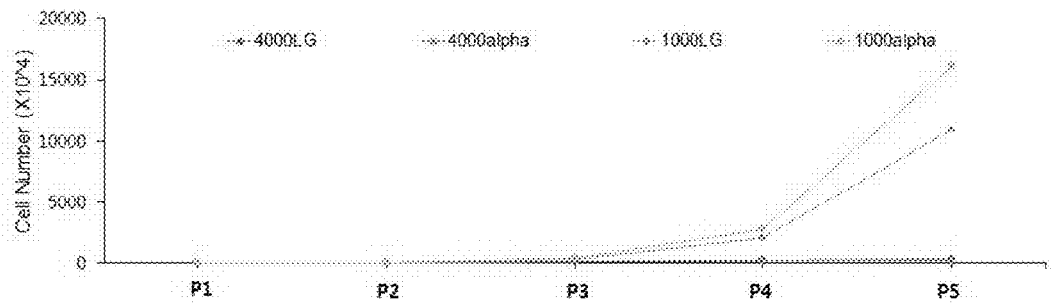
[FIG. 19B]
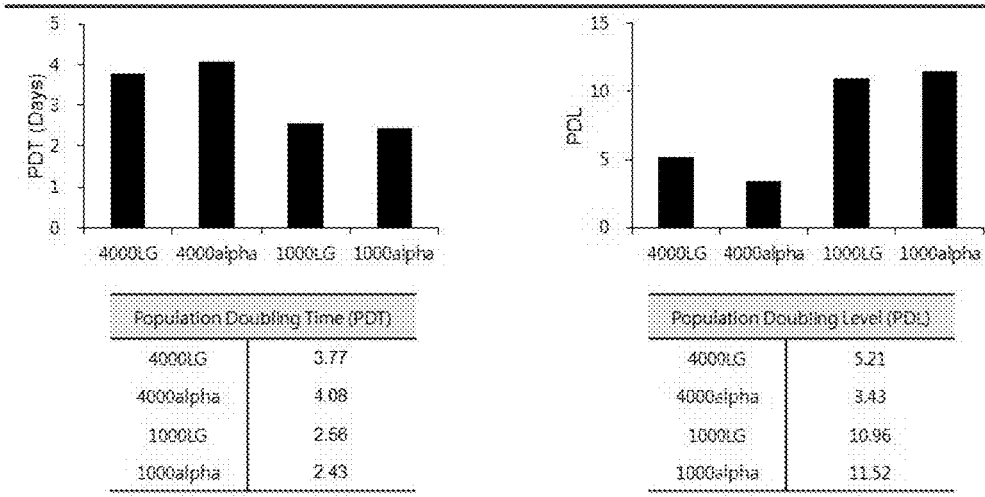
[FIG. 19]

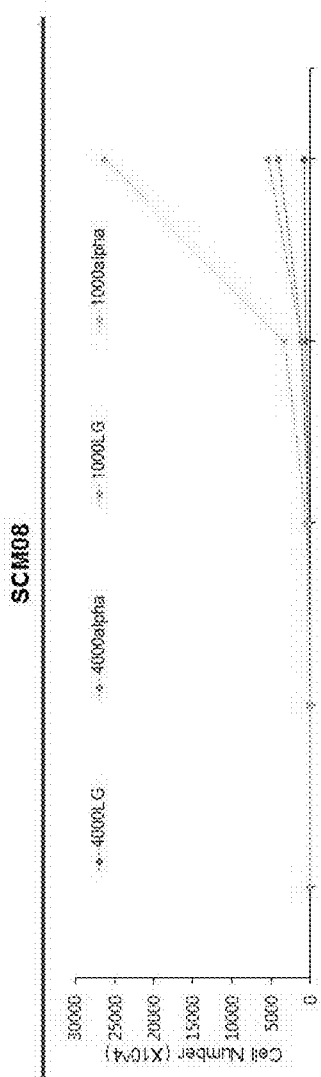
[FIG. 20A]
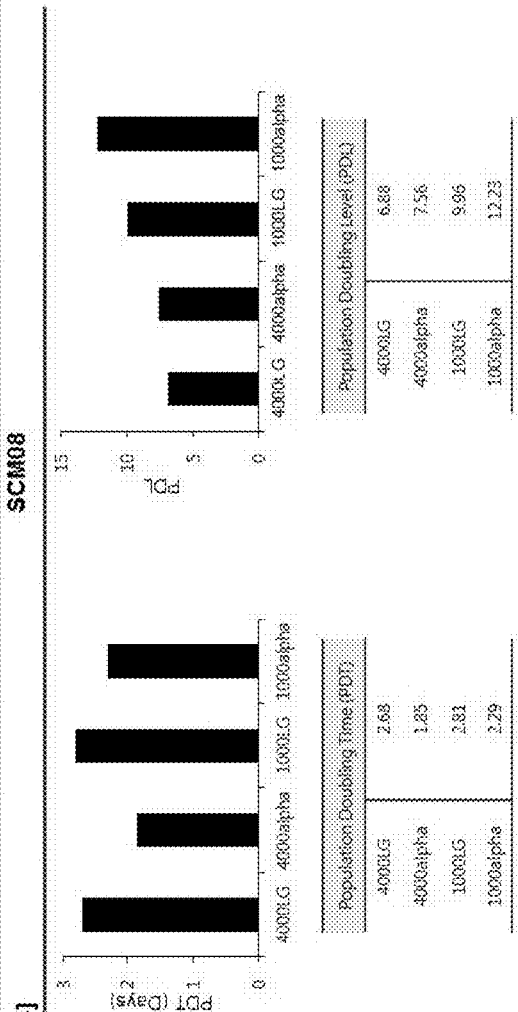
[FIG. 20B]
[FIG 20]

[FIG. 21]
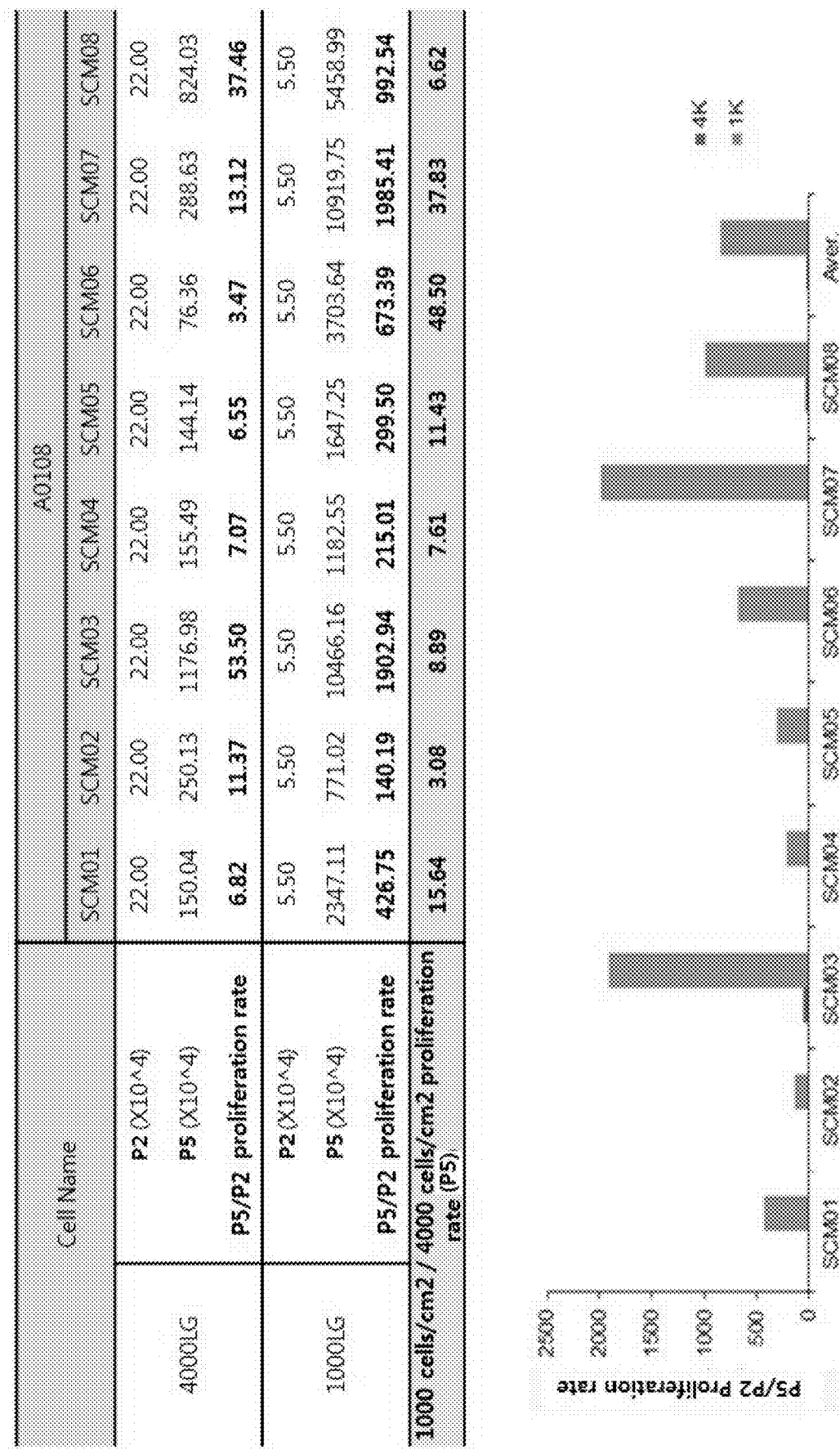

[FIG. 22]
| Cell Name | | A0108 | | | | | | | |
|---|---|---|---|---|---|---|---|---|---|
| | | SCM01 | SCM02 | SCM03 | SCM04 | SCM05 | SCM06 | SCM07 | SCM08 |
| PDT | 4000LG | 5.05 | 3.99 | 2.44 | 4.96 | 5.16 | 7.80 | 3.77 | 2.68 |
| | 1000LG | 3.20 | 3.93 | 2.57 | 3.61 | 3.40 | 2.98 | 2.56 | 2.81 |
| PDL | 4000LG | 3.84 | 5.12 | 7.55 | 4.18 | 4.42 | 2.54 | 5.21 | 6.88 |
| | 1000LG | 8.74 | 7.13 | 10.89 | 7.75 | 8.23 | 9.40 | 10.96 | 9.96 |
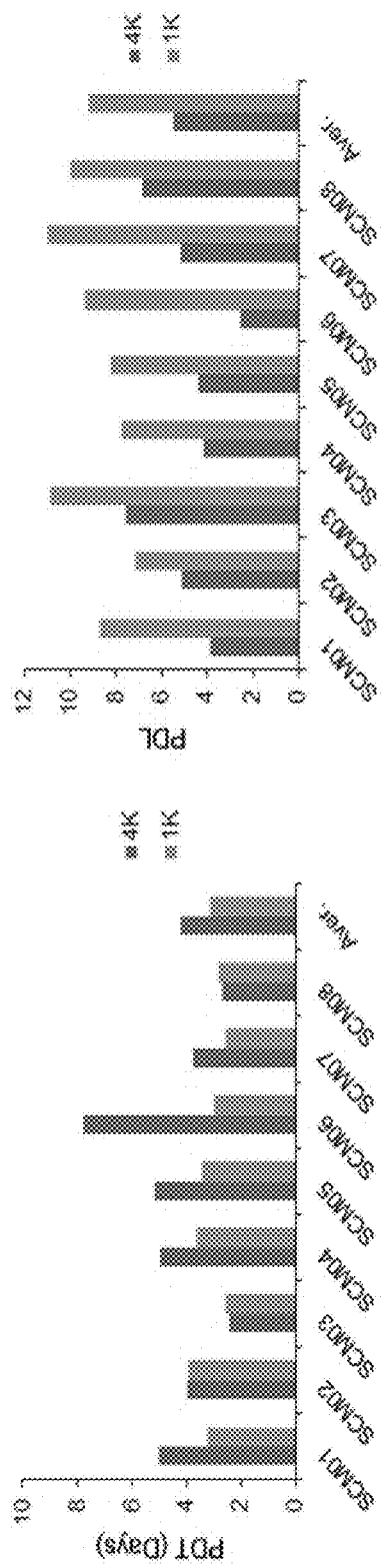

[FIG. 23]
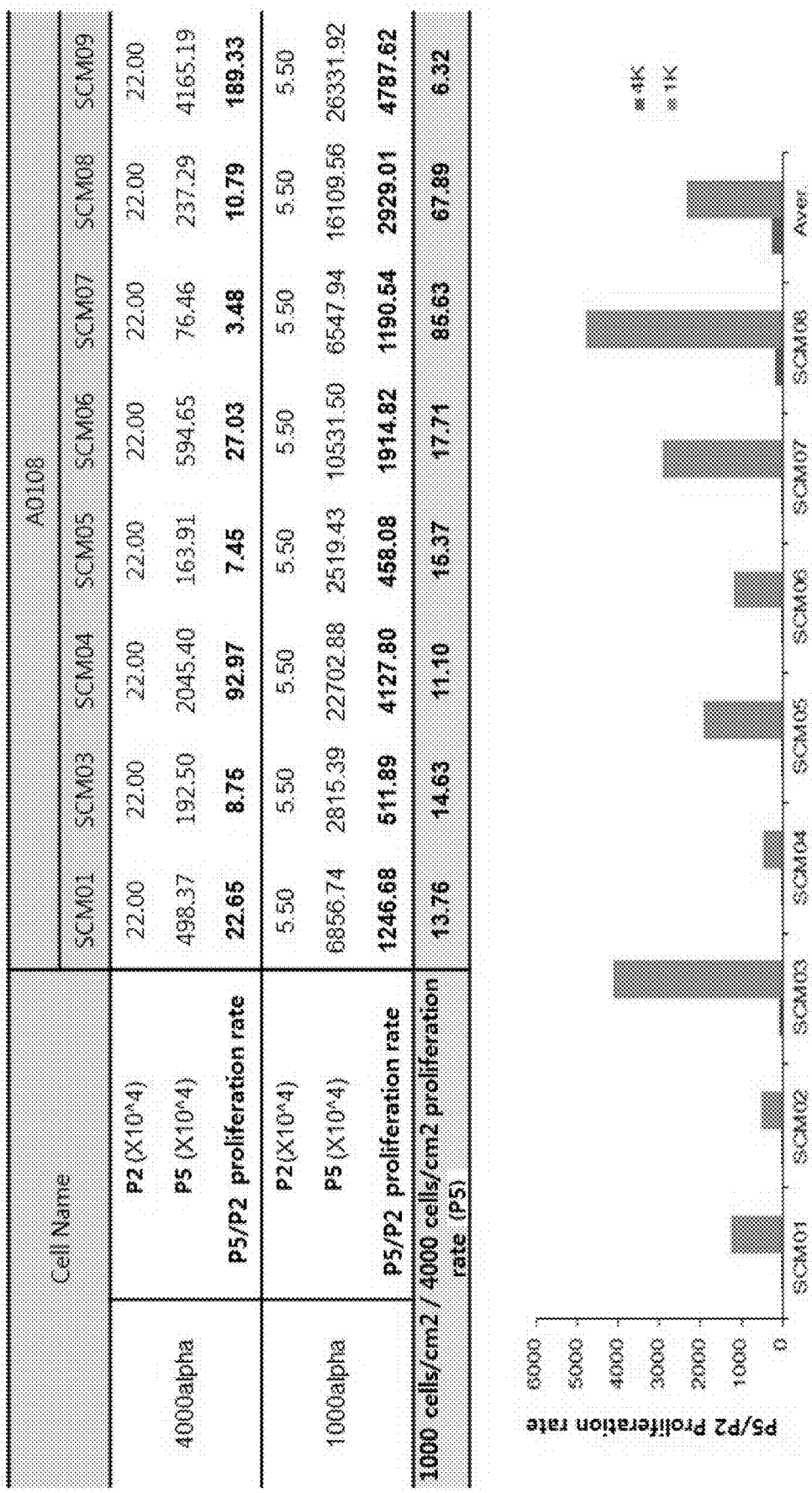

[FIG. 24]
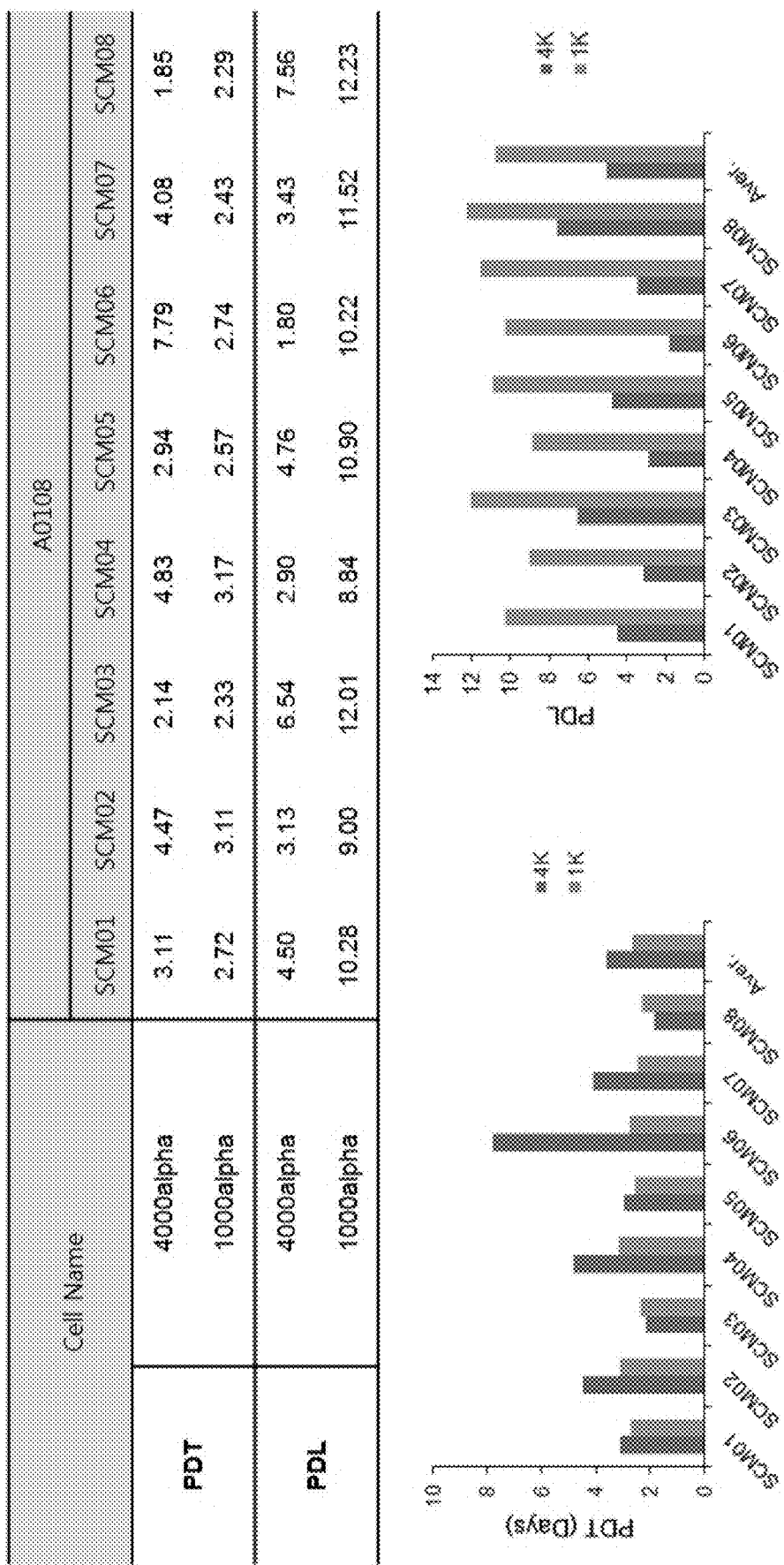

[FIG. 25]
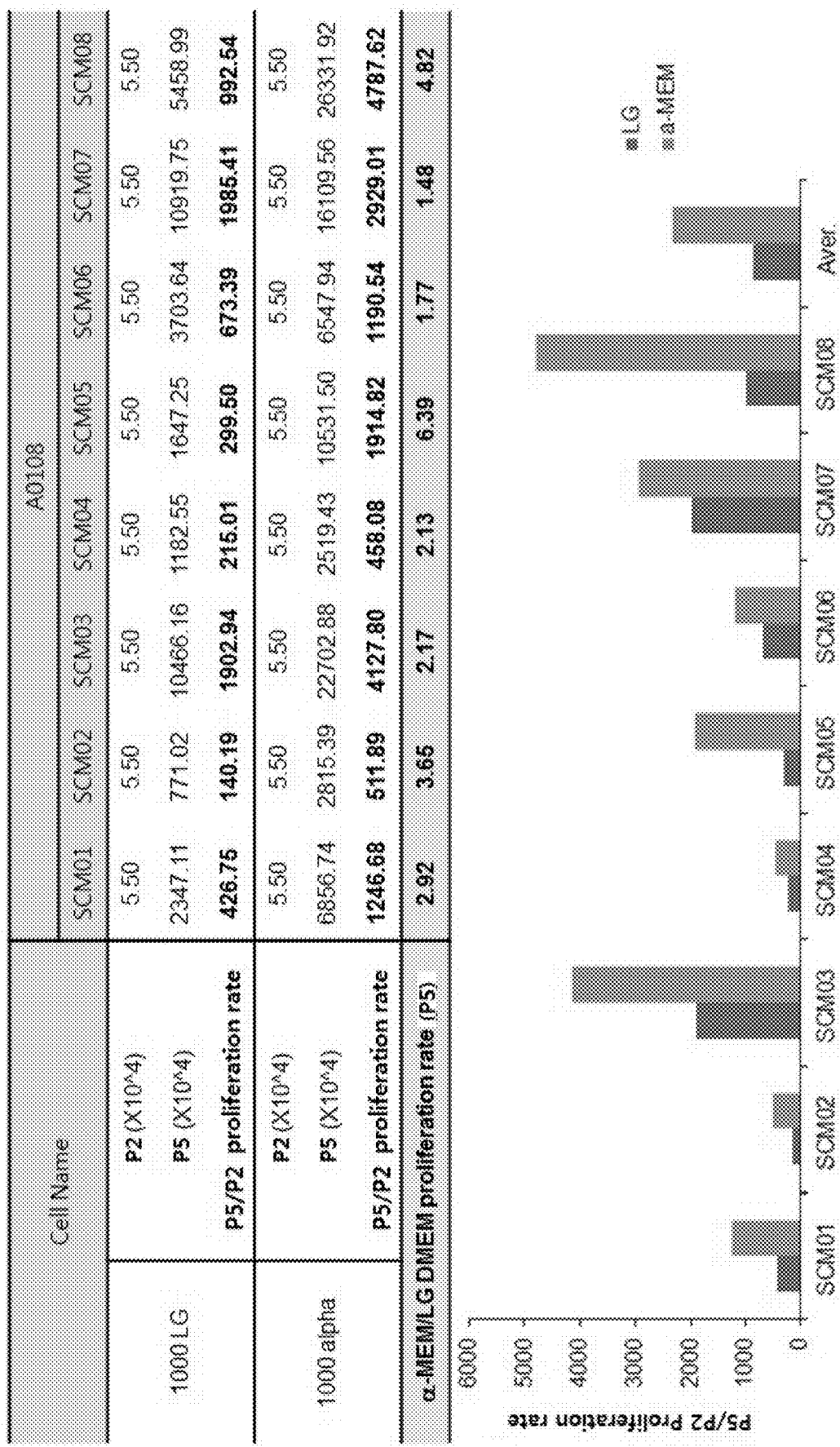

[FIG. 26]
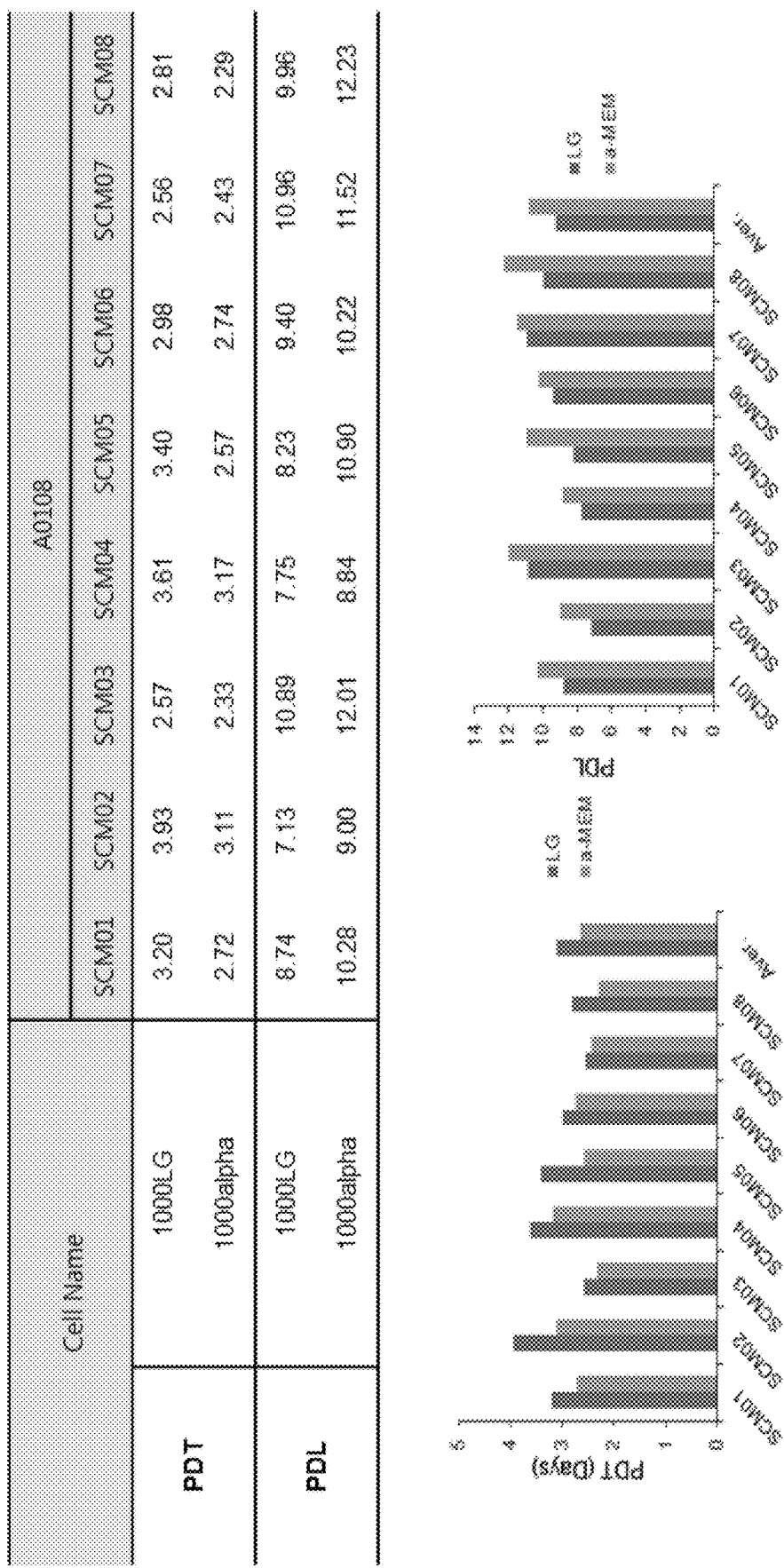

METHOD FOR ISOLATION OF STEM CELLS FROM BONE MARROW USING SUBFRACTIONATION CULTURING METHOD AND PROLIFERATION THEREOF

CROSS-REFERENCE TO RELATED APPLICATIONS

This application is based on and claims priority from Korean Patent Application No. 10-2017-0146906, filed on Nov. 6, 2017, with the Korean Intellectual Property Office, the disclosure of which is incorporated herein in its entirety by reference.

TECHNICAL FIELD

The present disclosure relates to a subfractionation culturing method of a stem cell and proliferation method of a monoclonal stem cell obtained using the same.

BACKGROUND

Stem cells have potential to grow into tissues of all 210 organs in our body, which can be infinitely divided and can be differentiated into desired organs by the suitable manipulation. Stem cells are new emerging therapeutic agents due to such characteristics. Further, it is expected that stem cells are used because of the high possibility of treatment of intractable diseases, thereby curing various diseases such as leukemia, osteoporosis, hepatitis, Parkinson's disease, senile dementia, and burn.

However, stem cells still have many obstacles because it is difficult to obtain the same in large scale. Although the method of obtaining stem cells from frozen embryonic cells may be efficient, there is still much controversy in terms of ethics. In order to address these issues, many studies have been conducted to obtain stem cells using somatic-cell nuclear transfer or adult stem cells. Studies on adult stem cells are more actively conducted compared with those on embryonic stem cells. Adult stem cells are present in various organs such as central nervous system and bone marrow to participate in the organ development during the growth period and the regeneration of damage. Thus, they can be obtained from various sites such as bone marrow, spleen and fat cells. However, bone marrow is the most common source. Meanwhile, it is difficult to obtain uniformly shaped cells at all times while mesenchymal stem cells among many kinds of bone marrow cells are isolated and cultured. Thus, studies are conducted to address these issues.

The separation method using Friedenstein et al., is still widely used, which is a method in which only mononuclear cells are isolated at the initial stage of division using the method called Ficoll-paque and attached to a culture vessel. However, these methods cause irregular cell characteristics and do not create single cell group because mesenchymal stem cells are present with other mononuclear cells together. Therefore, several studies were devised to obtain more identical cells. Luria et al.'s method isolated all cells attached to the bottom of the culture vessel but had the disadvantage of being able to isolate other stem cells rather than the mesenchymal stem cells (Luria et al., Transfusion, 11: 345-349, 1971). Simmons et al.'s method used an antibody using a specific antibody against Sca-1 and STRO-1 among the mesenchymal stem cell surface antigens so that there are always a high cost and contamination problem (Simmons et al., Blood, 78: 55-62, 2002). Hung et al.'s method is a mesenchymal stem cell separation method using the difference in cell size, which is also disadvantageous in that the purity of mesenchymal stem cells is not constant and that other stem cells can be mixed (Hung et al., Stem Cells, 20: 249-258, 2002).

In order to solve the above problems, the present inventors newly invented a method of isolating stem cells named as "subfractionation culturing method." The present inventors applied the method for patent by Korean Patent Application No. 10-2006-0075676, and the patent application was granted. The subfractionation culturing method can be carried out at a lower cost than other methods. In addition, there is no contamination problem, and monoclonal mesenchymal stem cells (MSCs) can be obtained efficiently without the possibility of combining other stem cells. Thus, it has a great superiority over other methods of obtaining stem cells.

The present inventors designed a novel subfractionation culturing method (SCM), obtaining single cell-derived monoclonal MSCs from mouse and human cells, which needs no centrifugation or enzymatic degradation. The principle of the subfractionation culturing method consists in isolating MSCs based on cell density and culture plate attachment.

However, in spite of the superiority of the method, the subfractionation culturing method has limitations in which it is difficult to rapidly obtain the monoclonal mesenchymal stem cell group. These are because in order to mass-produce monoclonal MSCs to be used as a final product, the method requires production of a working cell bank which is used for carrying out the process of obtaining the final product, thereby obtaining a sufficient amount of monoclonal mesenchymal stem cells and needs the culture with passage 10 to passage 12.

SUMMARY

The present disclosure has been made in an effort to improve the subfractionation culturing method to induce rapid proliferation of monoclonal stem cells. Therefore, the present inventors have found that the culture density of monoclonal stem cells was lowered, and the culture medium was supplemented with an antioxidant, thereby inducing an effective increase in cell proliferation rate. The present inventors have completed the present disclosure thereby.

Therefore, the purpose of the present disclosure is to provide a subfractionation culturing method and a proliferation method of stem cells, which improves conventional subfractionation culturing methods in the art.

An exemplary embodiment of the present disclosure provides a subfractionation culturing method of a stem cell and proliferation thereof, the method including: the steps of 1) culturing bone marrow isolated from an individual; 2) transferring the only supernatant of step 1) to a new container and culturing the supernatant; 3) separating the only supernatant of step 2), culturing the supernatant in a culture vessel at 37° C. for 1 hour to 3 hours, repeating culture of the supernatant at 37° C. for 12 to 36 hours 2 to 3 times, then culturing the supernatant at 37° C. for 24 to 72 hours, in which each supernatant is transferred to a new culture vessel to repeat the culture; 4) obtaining a monoclonal stem cell in the final culture vessel; and 5) inoculating the monoclonal stem cell in a culture medium at a cell density of 50 to 1000 cells/cm$^2$ to culture the cell.

According to the subfractionation culturing method of stem cells and the proliferation thereof of the exemplary embodiments of the present disclosure, it is advantageous that monoclonal stem cells may be quickly obtained without contamination, and a large amount of desired monoclonal stem cells may be obtained in a short time through the rapid proliferation, thereby being used for the preparation of stem cell-therapeutic agents.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a view of illustrating a subfractionation culturing method for isolating mesenchymal stem cells from human bone marrow;

FIG. 2 illustrates the results obtained by a microscope for the morphological changes of mesenchymal stem cells according to cell culture density and cell culture passage;

FIG. 3A illustrates the results of FACS analysis of the cell size and granularity of mesenchymal stem cells in means of FSC according to cell culture density and cell culture passage ($*p<0.05$, $p<0.01$ and $*p<0.005$);

FIG. 3B illustrates the results of FACS analysis of the cell size and granularity of mesenchymal stem cells in means of SSC according to cell culture density and cell culture passage ($*p<0.05$, $p<0.01$ and $*p<0.005$);

FIG. 4 illustrates the results of confirming whether cells are aged after staining mesenchymal stem cells by beta-gal-staining in which cell culture densities and cell culture passages varies;

FIG. 5 illustrates the results of RT-PCR of P15 and P16 which are age-related genes and PCNA which is a proliferation marker obtained after culturing the mesenchymal stem cells of passage 15 while the cell culture density varies;

FIG. 6 illustrates the results of confirming the proliferation ability of mesenchymal stem cells through population doubling time (PDT) and population doubling level (PDL) according to cell culture density and cell culture passage ($*p<0.05$, $p<0.01$ and $*p<0.005$);

FIG. 7 illustrates the results of confirming the differentiation capacity of mesenchymal stem cells according to cell culture density and cell culture passage ($*p<0.05$, $p<0.01$ and $*p<0.005$);

FIG. 7A illustrates the results of confirming the differentiation capacity of mesenchymal stem cells into lipocytes through Oil red O histological staining according to cell culture density and cell culture;

FIG. 7B is a view illustrating the results of quantifying the level of histological staining described FIG. 7A;

FIG. 7C illustrates the results of confirming the differentiation capacity of mesenchymal stem cells into osteogenic cells through Alizarin red S histological staining according to cell culture density and cell culture passage;

FIG. 7D is a view illustrating the results of quantifying the level of histological staining described in FIG. 7C;

FIG. 8A is a view illustrating total ROS production of mesenchymal stem cells according to cell culture density and cell culture passage;

FIG. 8B is a view illustrating the results of comet assay on DNA damage caused by total ROS production according to cell culture density and cell culture passage ($*p<0.05$, $p<0.01$ and $*p<0.005$);

FIG. 9 is a view illustrating the results of measuring 8-OHdG (8-hydroxy-deoxyguanosine) concentration in order to confirm the degree of DNA damage by ROS produced according to cell culture density and cell culture passage ($*p<0.05$, $p<0.01$ and $*p<0.005$);

FIG. 10 illustrates the results of confirming the changes in the proliferation ability of cells obtained by culturing the mesenchymal stem cells of passages 11 to 15 under the condition of only high density (HD) and high density+ ascorbic acid (HD+AA);

FIG. 11 illustrates the results of comparing levels of ROS produced by culturing the mesenchymal stem cells of passages 11 to 15 under the condition of only high density (HD) and high density+ascorbic acid (HD+AA) ($*p<0.05$, $p<0.01$ and $*p<0.005$);

FIG. 12 is a schematic diagram illustrating an experiment for improving the subfractionation culturing method;

FIG. 13 illustrates the results of confirming proliferation rate of cells in which SCM01 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 13A illustrates changes in cell numbers according to passage 1 (P1) to passage 5 (P5) of each experimental group;

FIG. 13B illustrates the results of PDT and PDL of each experimental group;

FIG. 14 illustrates the results of confirming proliferation rate of cells in which SCM02 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 14A illustrates changes in cell numbers according to passage 1 (P1) to passage 5 (P5) of each experimental group;

FIG. 14B illustrates the results of PDT and PDL of each experimental group;

FIG. 15 illustrates the results of confirming proliferation rate of cells in which SCM03 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 15A illustrates changes in cell numbers according to passage 1 (P1) to passage 5 (P5) of each experimental group;

FIG. 15B illustrates the results of PDT and PDL of each experimental group;

FIG. 16 illustrates the results of confirming proliferation rate of cells in which SCM04 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 16A illustrates changes in cell numbers according to passage 1 (P1) to passage 5 (P5) of each experimental group;

FIG. 16B illustrates the results of PDT and PDL of each experimental group;

FIG. 17 illustrates the results of confirming proliferation rate of cells in which SCM05 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 17A illustrates changes in cell numbers according to passages 1 (P1) to 5 (P5) of each experimental group;

FIG. 17B illustrates the results of PDT and PDL of each experimental group;

FIG. 18 illustrates the results of confirming proliferation rate of cells in which SCM06 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 18A illustrates changes in cell numbers according to passage 1 (P1) to passage 5 (P5) of each experimental group;

FIG. 18B illustrates the results of PDT and PDL of each experimental group;

FIG. 19 illustrates the results of confirming proliferation rate of cells in which SCM07 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 19A illustrates changes in cell numbers according to passages 1 (P1) to 5 (P5) of each experimental group;

FIG. 19B illustrates the results of PDT and PDL of each experimental group;

FIG. 20 illustrates the results of confirming proliferation rate of cells in which SCM08 monoclonal mesenchymal stem cells obtained by the subfractionation culturing method are inoculated at the density of 1000 or 4000 cells/cm$^2$, and the cells are cultured using LG-DMEM and α-MEM culture medium with or without an antioxidant;

FIG. 20A illustrates changes in cell numbers according to passage 1 (P1) to passage 5 (P5) of each experimental group;

FIG. 20B illustrates the results of PDT and PDL of each experimental group;

FIG. 21 illustrates the results of confirming the cell proliferation rate of an experimental group in which LG-DMEM without an antioxidant is used, and the cell density varies at the density of 1000 or 4000 cells/cm$^2$;

FIG. 22 illustrates the results of confirming PDT and PDL of an experimental group in which LG-DMEM without an antioxidant is used, and the cell density varies at the density of 1000 or 4000 cells/cm$^2$;

FIG. 23 illustrates the results of confirming the cell proliferation rate of an experimental group in which α-MEM with an antioxidant is used, and the cell density varies at the density of 1000 or 4000 cells/cm$^2$;

FIG. 24 illustrates the results of confirming PDT and PDL of an experimental group in which α-MEM with an antioxidant is used, and the cell density varies at the density of 1000 or 4000 cells/cm$^2$;

FIG. 25 illustrates the results of confirming the cell proliferation rate of an experimental group in which the cell density is fixed at the density of 1000 cells/cm$^2$, and the culture medium is LG-DMEM or α-MEM; and FIG. 26 illustrates the results of confirming PDT and PDL of an experimental group in which cell density is fixed at the density of 1000 cells/cm$^2$, and the culture medium is LG-DMEM or α-MEM.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure provides a subfractionation culturing method of mesenchymal stem cells and proliferation thereof.

The method of the present disclosure improves conventional subfractionation culturing methods, which has advantages that monoclonal stem cells, preferably monoclonal mesenchymal stem cells, may be quickly obtained without contamination, and a large amount of desired monoclonal stem cells may be obtained in a short time through the rapid proliferation of monoclonal stem cells, preferably monoclonal mesenchymal stem cells.

Hereinafter, the present disclosure is described in detail.

The present disclosure provides a subfractionation culturing method of a stem cell and proliferation thereof, the method including: the steps of 1) culturing bone marrow isolated from an individual; 2) transferring the only supernatant of step 1) to a new container and culturing the supernatant; 3) separating the only supernatant of step 2), culturing the supernatant in a culture vessel at 37° C. for 1 hour to 3 hours, repeating culture of the supernatant at 37° C. for 12 to 36 hours 2 to 3 times, then culturing the supernatant at 37° C. for 24 to 72 hours, in which each supernatant is transferred to a new culture vessel to repeat the culture; 4) obtaining a monoclonal stem cell in the final culture vessel; and 5) inoculating the monoclonal stem cell in a culture medium at a cell density of 50 to 1000 cells/cm$^2$ to culture the cell.

Steps 1) to 3) may be performed in the same method as the subfractionation culturing method described in Korean Patent Application No. 10-2006-0075676, and Korean Patent Application No. 10-2006-0075676 can be incorporated herein in its entirety by reference.

The term "subfractionation culturing method" used herein refers to a method of isolating stem cells according to specific gravity, indicating a process in that first, human bone marrow is extracted and cultured in a cell culture medium, then, only a supernatant is obtained, transferred to a culture vessel with or without treatment of a coating agent, and cultured, and then the processes as described above are repeated several times. Such a subfractionation culturing method is characterized by repeatedly obtaining and culturing the supernatant without centrifugation. It is advantageous that monoclonal stem cells, preferably monoclonal mesenchymal stem cells can be obtained without contamination of other cells finally.

The culture in steps 2) and 3) is performed at 37° C. for 4 hours or less, preferably for 1 to 3 hours, more preferably for 1 hour 30 minutes to 2 hours and 30 minutes. The repeated culture is performed at 37° C. for 4 hours or less (preferably for 1 to 3 hours, more preferably for 1 to 30 minutes to 2 hours and 30 minutes) then is performed at 37° C. for 12 to 36 hours (preferably for 18 to 30 hours) to be repeated 2 or 3 times. Further culture is carried out 37° C. for 24 to 72 hours (preferably for 36 to 60 hours). Each supernatant can be transferred to a new culture vessel to perform the next experiment. According to one embodiment of the present disclosure, a brief summary of the isolation method is as follows.

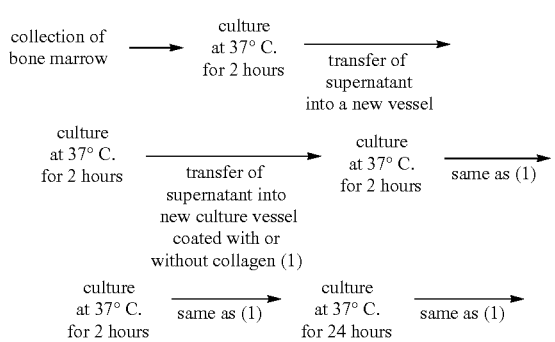

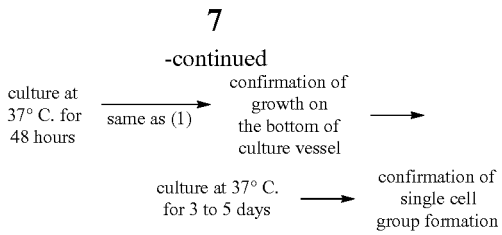

The cultured cells are formed to as monoclonal cell groups. These monoclonal cell groups may be isolated and subcultured. The present disclosure includes step 5) of culture so as to rapidly collect the monoclonal stem cells in large quantities, which can be obtained through the subfractionation culturing method.

Step 5) is a process of inoculating monoclonal stem cells into a culture medium at a cell density of 1000 cells/cm$^2$ or less, preferably 50 to 1000 cells/cm$^2$.

The culture may preferably be passage 1 to passage 5. The present disclosure can induce rapid proliferation of monoclonal stem cells so that a final product can be obtained rapidly. Further, a master cell bank (MCB) may be prepared through the culture of passage 1 to passage 5.

When a density of the monoclonal stem cells of the present disclosure excesses 1000 cells/cm$^2$ so that the monoclonal stem cells are cultured at a high density of 4000 cells/cm$^2$ as in the conventional method, the cell proliferation ability may be markedly decreased, the markers of the mesenchymal stem cells may be changed, and the differentiation ability may be eliminated. Thus, the monoclonal stem cells obtained through the subfractionation culturing method may be cultured at a low density or intermediate density, that is, at the cell density of 1000 cells/cm$^2$ or less, preferably at the cell density of 50 to 1000 cells/cm$^2$, more preferably at the cell density of 1000 cells/cm$^2$.

When monoclonal mesenchymal stem cells are cultured at a cell density of 1000 cells/cm$^2$ or less, the cell proliferation ability is remarkably high over an extended period of culture compared with mesenchymal stem cells cultured at a high density of 4000 cells/cm$^2$. Thus, it provides an advantage that a large amount of monoclonal cells which is desired can be rapidly obtained without repeating a large number of passages. Further, when the monoclonal mesenchymal stem cells are cultured at the above-mentioned cell density, the cells have the advantage that their DNA may be less damaged, and they are less aged, thereby effectively maintaining the differentiation ability of the stem cells. Thus, monoclonal mesenchymal stem cells can be rapidly and quickly obtained to have excellent stem cell properties.

The medium used in the present disclosure may include a medium without an antioxidant, a medium supplemented with an antioxidant, or a medium containing an antioxidant.

The medium without an antioxidant may, but be not limited to, include DMEM. If necessary, an antioxidant can further be added to the medium to perform the culture. If necessary, α-MEM containing an antioxidant may be used to perform the culture.

The antioxidants of the present disclosure may include, without limitation, antioxidants that can be used in cell cultures. They may include one or more selected from the group consisting of glutathione, cysteine, cysteamine, ubiquinol, beta-mercaptoethanol and ascorbic acid. When the medium is supplemented with an antioxidant, the antioxidant may be added at a concentration of 10 to 50 μg/ml, preferably 10 to 30 μg/ml, and more preferably 25 μg/ml.

In one embodiment of the present disclosure, DMEM, more preferably LG-DMEM, is used as a medium without an antioxidant, and α-MEM is used as a medium containing ascorbic acid as an antioxidant.

Meanwhile, according to the method of the present disclosure, the monoclonal stem cells may be proliferated very effectively, thereby excluding a process of producing a working cell bank (WCB) using MCB. This results in more simplified method compared with the conventional subfractionation culturing method in which WCB should be prepared after MCB is prepared.

The culture of step 5) of the present disclosure may be characterized by culturing at a cell density of 1000 cells/cm$^2$ or less during the passage 1 to passage 5. Preferably, monoclonal stem cells are inoculated and cultured in the medium at a cell density of 50 to 1000 cells/cm$^2$ during passage 1. After the cells are proliferated, the monoclonal stem cells are inoculated and cultured in the medium at a cell density of 1000 cells/cm$^2$ or less during passage 2 to passage 5, more preferably 700 to 1000 cells/cm$^2$, and even more preferably 1000 cells/cm$^2$.

The present disclosure may use a medium with an antioxidant as a culture medium. The culture medium may be added with gentamicin as an antibiotic.

The mesenchymal stem cells obtained by the method of the present disclosure may finally be mesenchymal stem cells of passage 5 to passage 10, preferably the mesenchymal stem cells of passage 6 to passage 8. This is a lower passage number compared with the conventional process in which the results are mesenchymal stem cells obtained by at least passage 10 to passage 12, demonstrating that the cell inoculation density is controlled to easily obtain a large number of the mesenchymal stem cells rapidly proliferated in the low passage.

The mesenchymal stem cells obtained may be not only monoclonal stem cells obtained by the subfractionation culturing method but also mesenchymal stem cells of effectively maintaining their differentiation ability. In particular, monoclonal stem cells cultured at a cell density of 1000 cells/cm$^2$ or less may maintain their bone cell differentiation ability efficiently compared with those cultured at a high density of more than 1000 cells/cm$^2$.

Hereinafter, the present disclosure is described in detail with accompanying Examples.

The following Examples are only intended to illustrate the present disclosure but do not limit to the contents of the present disclosure.

Example 1

Analysis of Mesenchymal Stem Cells According to Cell Density

In order to provide a further improved subfractionation culturing method of a stem cell and proliferation thereof compared with the subfractionation culturing method described in Korean Patent Application No. 10-2006-0075676, the cell density and culture medium were varied in the culture conditions. Accordingly, the characteristics of mesenchymal stem cells obtained were compared and analyzed.

In the experiments as below, the cell culture densities of the monoclonal mesenchymal stem cells (MSCs) obtained by the subfractionation culturing method were varied in 50 cells/cm$^2$ (low density), 1000 cells/cm$^2$ (medium density) and 4,000 cells/cm$^2$ (high density), thereby analyzing the characteristics of the cells.

1.1 Confirmation of Morphological Changes of MSC According to Cell Density

First, the experiments were conducted to confirm the morphological changes of MSCs according to cell density in long-term culture. The MSCs having passage 5 (P5), passage 10 (P10) and passage 15 (P15) were used for the long-term culture conditions. The MSCs were inoculated in DMEM under the condition of low density, medium density and high density, respectively. Thereafter, the morphological changes of the cells were observed through a microscope to determine whether or not the stem cells were aged. The results are illustrated in FIG. 2.

As illustrated in FIG. 2, the cell size and morphological pattern of P5 and P10 were different according to the cell density. In particular, P15 cultured under a high density culture condition had flat and enlarged MSCs. This morphology form indicates the typical aging of MSCs, which confirms that the cell density is controlled in the long-term culture, resulting in the control of MSC's aging.

1.2 Confirmation of MSC Size and Granularity According to Cell Density

In order to further confirm the change of stem cells according to the cell density, the cell size and granularity, which were known to be increased in aged cells, were analyzed by FACS analysis. Thus, the results are illustrated in FIG. 3.

As illustrated in FIG. 3, the cell size did not show a significant difference at P5, but P10 and P15 showed significant differences according to the cell density. In particular, the cell sizes in P10 and P15 were significantly increased under a culture condition of the high cell density, thereby further promoting aging of cells. Similarly, the cell granularity also was significantly increased as the cell density was increased in all passages. Therefore, controlling cell density of MSC in long-term culture can be a factor to control aging of cells. Further, the cell culture density is lower to improve the morphological changes in the late passage.

1.3 Confirmation of Aging of MSC According to Cultured Cell Density

The beta-gal-staining analysis was performed to confirm whether the morphological changes confirmed in Examples 1.1 and 1.2 were actually an age-dependent phenomenon of MSC, which can selectively stain aging cells, and RT-PCR was carried out to compare the expression of aging-related genes P15, P16 and PCNA gene, a proliferation marker. The results are illustrated in FIGS. 4 and 5, respectively.

As illustrated in FIG. 4, P5 and P10 did not have the staining of aged cells at all cell densities, but P15 had the staining of aged cells markedly increased as the cell density increased. As illustrated in FIG. 5, in P15, gene expression of CDK inhibitors P15 and P16, which are genes related to aging, was increased as the cell density increased, and PCNA, which is a proliferation marker, decreased.

These results demonstrate that the morphological changes of MSCs are related to the aging of MSCs and that the manipulation of the cell density can control the aging of MSCs.

1.4 Confirmation of Change of Proliferation Ability of MSCs According to Culture Cell Density It is known that the proliferation ability of MSCs progressively decreases as cells are subcultured and aged. Therefore, the proliferation ability can be used as a criterion for confirming the aging of MSCs. Thus, the proliferation ability of MSCs according to the cell culture density was compared during long-term cell culture. The proliferation ability of each cell was determined by calculating the proliferation rate according to each passage using the number of cells which were initially inoculated and the number of cells which were obtained after the culture. The results are shown in Table 1 and FIG. 6.

TABLE 1

| (cells/cm$^2$) | Fold increase | | |
|---|---|---|---|
| | P5 | P10 | P15 |
| 50 | 88.4 ± 6.5 | 34.3 ± 5.0 | 16.4 ± 1.3 |
| 1000 | 8.5 ± 0.3 | 4.9 ± 0.5 | 3.1 ± 0.4 |
| 4000 | 3.0 ± 0.1 | 1.9 ± 0.1 | 1.1 ± 0.1 |

As shown in Table 1, the fold increases were 88.4, 34.3 and 16.4 at P5, P10 and P15, respectively, in MSCs cultured at a low density. Meanwhile, the fold increases in MSCs cultured at a medium density were 8.5, 4.9 and 3.1 at P5, P10 and P15, respectively. Further, the fold increases were 3.0, 1.9, and 1.1 at P5, P10 and P15, respectively, in MSCs cultured at a high density. As illustrated in FIG. 6, the PDT and the PDL also have the same pattern as the fold increase. These results indicate that the proliferation ability of MSCs can be maintained by lowering the cell density in long-term MSC culture and that even though performing the same subculture, the aging of MSCs may be inhibited and the lifespan of MSCs may be prolonged.

1.5 Confirmation of Change of Differentiation Potential of MSCs According to Culture Cell Density The differentiation potentials according to P5 to P15 cultures were compared to confirm whether culture cell density affects the ability of stem cells. The ability of stem cells to differentiate into adipocytes and osteocytes was confirmed. Qualitative and quantitative analyzes were carried out at each passage and density. Specifically, NCS (Newborn Calf Serum) (Gibco), $10^{-7}$ mol dexamethasone (Sigma), 0.5 mM IBMX (Sigma), 10 µg/ml insulin (Sigma), and 100 µM indomethacin (Sigma) were added to a high glucose DMEM culture medium to prepare the adipocyte differentiation medium, and then the experiment was carried out. After 7 days of differentiation, it was confirmed by Oil red O histochemical staining. After the Oil red O histochemical staining, it was eluted with isopropyl alcohol and measured at 500 nm and quantitatively analyzed.

The osteoclast differentiation medium was prepared and used by adding FBS (Gibco), 50 µg/ml ascorbic 2-phosphate (Sigma), $10^{-8}$ mol dexamethasone (Sigma) and 10 mM β-glycerophosphate (Sigma) to α-MEM. After 21 days of differentiation, it was confirmed by Alizarin red S histochemical staining. After Alizarin red S histochemical staining, it was eluted with 10% acetic acid, measured at 405 nm and quantitatively analyzed. The adipocyte differentiation ability and the osteoclast differentiation ability were confirmed as described above. The results are illustrated in FIG. 7.

As illustrated in FIG. 7, the adipocyte differentiation potential decreased overall as the passage progressed, but the difference according to the density was not apparent. On the other hand, the osteoclast differentiation potential significantly decreased in the P15 culture group under the condition of high density. These results show that the osteoclast differentiation potential of MSCs can be maintained better when culturing at a low cell density.

1.6 Antigen Profile Analysis of MSCs According to Culture Cell Density

Experiments were carried out to confirm whether or not the cell culture density also affects the stem cell antigen expression. Flow cytometry was performed to confirm the changes in positive and negative antigen expression according to each passage and culture density. The results are shown in Table 2.

TABLE 2

| | | Passage | | | | | | | | |
|---|---|---|---|---|---|---|---|---|---|---|
| | | P5 | | | P10 | | | P15 | | |
| | | Density | | | | | | | | |
| | | LD | MD | HD | LD | MD | HD | LD | MD | HD |
| Positive | CD29 | 98.8 | 97.8 | 99.7 | 96.2 | 99.2 | 94.2 | 87.3 | 97.8 | 48.5 |
| | CD44 | 95.2 | 95.4 | 99.6 | 94.6 | 75.8 | 72.7 | 93.8 | 80.6 | 31.4 |
| | CD73 | 71.7 | 78.9 | 80.8 | 86.8 | 31.2 | 22.3 | 60.3 | 20.9 | 3.8 |
| | CD90 | 99.5 | 98.6 | 99.4 | 92.2 | 98.7 | 95.2 | 94.9 | 98.5 | 86.0 |
| | CD105 | 63.9 | 71.0 | 30.6 | 59.0 | 49.8 | 44.1 | 15.7 | 3.5 | 4.4 |
| | CD146 | 61.0 | 24.9 | 28.5 | 37.2 | 42.0 | 16.6 | 33.8 | 18.9 | 4.9 |
| Negative | CD31 | 2.7 | 3.8 | 4.0 | 1.6 | 3.8 | 3.9 | 1.6 | 2.7 | 3.2 |
| | CD104 | 2.1 | 3.6 | 4.0 | 1.5 | 4.6 | 4.2 | 2.6 | 3.8 | 2.1 |
| | HLA-DR | 2.8 | 3.0 | 3.6 | 2.4 | 4.5 | 4.0 | 2.1 | 3.4 | 2.8 |
| | CD14 | 3.2 | 3.9 | 4.0 | 3.3 | 5.8 | 4.2 | 2.4 | 3.1 | 2.9 |

Representative data from two independent experiments are shown

As shown in Table 2, the change of the expression of the negative marker was not clearly apparent, but the expression level of some positive markers was changed according to the cell culture density even in the same passage. In particular, CD105 and CD146 exhibited a marked decrease in the expression level as the cell culture density increased. Further, the expression of CD73 tended to decrease significantly as the culture density increased in P10 or higher passage. In particular, when cells were cultured at a high density in P15, the expression level of most positive markers was significantly decreased. Further, CD73, CD105, and CD105 showed negative expression. Thus, cell culturing with a low cell density can be a critical factor.

1.7 Comparison of ROS Production and DNA Damage According to Culture Cell Density It is known that the decrease of mesenchymal stem cell function is associated with DNA damage. In particular, DNA damage induced by ROS, which is an active oxygen species, is known to promote aging of MSCs. Therefore, in order to confirm whether or not total ROS production and DNA damage caused thereby are different, fluorescence intensity analysis was performed to compare the total amount of cellular ROS according to passage and cell culture density. Comet analysis was performed to confirm the degree of DNA damage. The results are illustrated in FIG. 8.

As illustrated in FIG. 8, total ROS production tended to increase as the cell culture density increased in all passages. In particular, ROS production significantly increased at P10 and P15 (See FIG. 8A). In the comet analysis, the data were classified from CC1 with the weakest DNA damage to CC5 with the most severe DNA damage. The CC5 with the most severe DNA damage exhibited a significant increase as the cell culture density increased. On the other hand, the CC1 tended to decrease significantly as the cell density increased (See FIG. 8B).

Further, in order to confirm whether or not ROS caused DNA damage, an experiment was conducted to confirm the concentration of 8-OHdG which may identify DNA damage caused by ROS. The analysis of 8-OHdG is as follows. 50 μl the DNA sample collected from each cell was placed on an 8-OHdG conjugate coated plate and incubated at room temperature for 10 minutes. Then, an anti-8-OHdG antibody was added thereto and the mixture was incubated at room temperature for 1 hour. After washing three times, secondary antibody-enzyme conjugate was added to each well, and the mixture was incubated at room temperature for another 1 hour. After washing three times, a substrate solution was added thereto, and the mixture was incubated at room temperature for 30 minutes. Finally, a stop solution was added thereto. The absorbance intensity thereof was measured at 450 nm. The results are illustrated in FIG. 9.

As illustrated in FIG. 9, as the cell culture density increased, the concentration of 8-OHdG was significantly increased in P15 group in which DNA damage was most severe. These results demonstrate that ROS produced under the culture condition of the high density caused DNA damage to increase, thereby promoting aging of MSCs.

These results show that lowering the cell culture density may play a role in protecting MSCs from DNA damage which is caused by increased ROS production of MSCs.

1.8 Confirmation of MSC Proliferation and ROS Production Ability According to Antioxidant Treatment In order to confirm whether or not ROS produced under the culture condition of high density affects the proliferation of MSCs, an experiment for eliminating ROS was performed. 25 μl/ml ascorbic acid, an antioxidant, was added to the culture medium under the culture condition of high density in P11 to P15. Then, the fold increase of proliferation was compared between the two groups. The results are illustrated in FIG. 10.

As illustrated in FIG. 10, the fold increase was 2.6, 1.9, and 1.6 at P11 to P15 in the high density culture condition. As passage number increased, the proliferation ability decreased, and as a result, aging began. However, treating with the antioxidant induced to maintain high proliferation ability at about 50% in all passages. In the antioxidant treatment group, the growth fold increase was 3.8, 2.9 and 2.5 in P11 to P15, respectively. The proliferation ability was maintained high even at P15.

At the endpoint P15, ROS levels were confirmed between the high density culture condition alone and high density culture condition+antioxidant treatment group. The results are illustrated in FIG. 11.

As illustrated in FIG. 11, the ROS level also decreased under the condition that proliferation was increased by treating ascorbic acid, an antioxidant. Therefore, MSC culture was preferably performed at a low cell density rather than a high density. ROS production induced by a high density of cell culture was eradicated with an antioxidant, thereby resulting in an increase of MSC proliferation ability. In other words, ROS at a high density inhibited MSC proliferation ability. As the cell density was lower, the ROS production was decreased, and the MSC proliferation ability was promoted.

In conclusion, these results indicate that controlling the cell density at the density of 1000 cells/cm² or less in culture conditions is important to maintain the proliferation, culture and stem cell ability of the monoclonal mesenchymal stem cells obtained through the subfractionation culturing method. Culture with an antioxidant inhibits oxidative stress induced by cell culture, thereby promoting MSC proliferation efficiently.

Example 2

Verification of Improved Subfractionation Culturing Method

Example 1 has confirmed that the control of cell density and the addition of an antioxidant can be critical factors in the MSC culture obtained by the subfractionation culturing method. Therefore, the experiments were conducted to compare the proliferation ability of single colony MSCs and their effect of obtaining cells during varying the cell culture density of monoclonal mesenchymal stem cells obtained by the conventional method, the subfractionation culturing method described in Korean Patent Application No. 10-2006-0075676, and using a culture medium containing ascorbic acid as an antioxidant.

Korean Patent Application No. 10-2006-0075676 as previously disclosed, described that monoclonal cells were transferred to wells at 100 to 600 cells per well, and then were cultured at 4000 cells per cm² in their subculture.

Specifically, the present improvement provides a method of culturing cells to adjust the number of cells to be 1000 per cm² in passage 1 (P1), inducing effective proliferation of cells. Further, in the subculture after passage 2 (P2), cells are seeded on wells in 1000 cells or less which is a low density. These are compared with the effect of 4,000 cells culture. Further, α-MEM medium containing antioxidant and LG-DMEM medium containing no antioxidant are used as a cell culture medium, thereby comparing their effects of cell proliferation.

Experimental groups for confirming the effect of the improved subfractionation culturing method are shown in Table 3. The improved processes are schematically illustrated in FIG. 12.

TABLE 3

| Group | Culture density | Medium Condition | Passage | Subculturing Period (day) | Medium Change |
|---|---|---|---|---|---|
| 4000LG | 4000 cells/cm² | LG-DMEM | P2-P5 | 3-4 | X |
| 4000alpha | 4000 cells/cm² | alpha-MEM | | 3-4 | X |
| 1000LG | 1000 cells/cm² | LG-DMEM | | 7 | ○ (every 3-4 days) |
| 1000alpha | 1000 cells/cm² | alpha-MEM | | 7 | ○ (every 3-4 days) |

Cell lines were separated by the subfractionation culturing method, which are named as SCM01 to SCM08, respectively.

2.1 Confirmation of Proliferation Effect According to Cell Line Density and Medium The cells were cultured using the SCM01 to SCM08 cell lines. To confirm the cell proliferation effect according to subculture up to passage 5(P5), the cell number, population doubling time (PDT) and population doubling level (PDL) were compared, respectively. The results are illustrated in FIGS. 13 to 20.

As illustrated in FIGS. 13 to 20, the cell proliferation effect of all experimental groups inoculated and cultured with a cell density of 1000 cells per cm² was superior to those of experimental groups inoculated and cultured with a cell density of 4000 cells per cm². Furthermore, even in the same 1000 cell density group, the 1000-alpha experimental group cultured in α-MEM containing ascorbic acid as an antioxidant showed more significant cell proliferation effect than other groups.

2.2 Comparison of Proliferation Effect According to Cell Line Density

For a more accurate comparison of the proliferation rate according to the number of cultured cells, LG-DMEM and α-MEM, respectively, were set as a culture medium, and the inoculation density was set as 1000 and 4000 cells, respectively. Accordingly, the cell proliferation effect was compared. The results are illustrated in FIGS. 21 to 24.

As illustrated in FIG. 21, when the SCM01 to SCM08 cell lines inoculated with 1000 cells/cm² were cultured in LG-DMEM, the proliferation rate of P2 to P5 was significantly higher than that of the group inoculated with 4000 cells/cm². The proliferation rate of the group inoculated with 1000 cells/cm² was at least 3.08 to at most 48.50 times compared with those of the group inoculated with 4000 cells/cm² in passage 5 (P5). Further, as illustrated in FIG. 22, the PDT value was also lower or similar to those of 4000 cells/cm²inoculation in all cell lines, and the PDL value was higher than those of 4000 cells/cm² inoculation in all cell lines.

Further, as illustrated in FIG. 23, when all SCM01 to SCM08 cell lines cultured in α-MEM were inoculated and cultured with 1000 cells/cm², their tendency was similar to those of DMEM experimental groups. The proliferation rate of the group inoculated with 1000 cells/cm² was at least 6.32 to at most 85.63 times compared with those of the group inoculated with 4000 cells/cm² in passage 5 (P5). Further, as illustrated in FIG. 24, the PDT value was also lower or similar to those of 4000 cells/cm²inoculation in all cell lines, and the PDL value was higher than those of 4000 cells/cm² inoculation in all cell lines.

These results demonstrate that the inoculation with 1000 cells/cm² or less can induce rapid proliferation of monoclonal mesenchymal stem cells compared to high density cell line inoculation of 4000 cells per cm².

2.3 Comparison of Proliferation Effect According to Culture Medium

Example 2.2 confirmed that 1000 cells/cm² culture showed excellent proliferation effect compared with 4000 cells/cm² culture. Therefore, the experiment was conducted to compare the cell proliferation effect while the number of cells was set as 1000 cells/cm², and the medium varied as a variable. Thus, the proliferation effect was further verified according to the culture medium conditions. The results are illustrated in FIGS. 25 and 26.

As illustrated in FIG. 25, the cell proliferation rates were compared between α-MEM and DMEM. The results showed that the proliferation rate of the group using α-MEM was at least 1.77 to 6.39 times compared with those of the group using LG-DMEM. Further, as illustrated in FIG. 26, the PDT was low in all α-MEM groups and the PDL was increased in all α-MEM groups.

These results indicate that the cell proliferation efficiency can be maximized by culturing cells using a medium containing an antioxidant in addition to manipulation of the cell inoculation density of 1000 cells or less per cm$^2$ and culture of the cells in passage 2 (P2) to passage 5 (P5).

Example 3

Establishment of Improvement Process

Examples, as described above, confirmed that the control of cell density and the addition of an antioxidant might be important factors in the MSC culture. Based on the conventional subfractionation culturing method described in Korean Patent Application No. 10-2006-0075676, the improvement process was carried out by varying the cell culture density and the medium conditions for effectively obtaining single colony mesenchymal stem cells. These are collectively shown in the following Table 4 (culture conditions using DMEM) and Table 5 (culture conditions using α-MEM).

TABLE 4

| Process | Items | Fresh Product | Process A | Process B-1 (Frozen Product) | Process B-2 (Frozen Product) |
|---|---|---|---|---|---|
| Bone marrow to MCB | Culture medium | DMEM | DMEM | DMEM | DMEM |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) | Penicillin-streptomycin Penicillin (100 units/mL) Streptomycin (100 μg/mL) | Penicillin-streptomycin Penicillin (100 units/mL) Streptomycin (100 μg/mL) |
| | Cell culture density | 4000~5700 cells/cm$^2$ | 4000~5700 cells/cm$^2$ | 50~1000 cells/cm$^2$ | 50~1000 cells/cm$^2$ |
| | Subculturing period | 3~4 days | 3~4 days | 5~14 days | 5~14 days |
| | Medium change | X | X | ○ (every 3~4 days) | ○ (every 3~4 days) |
| | Subculture (Passage) | P1~P5 | P1~P5 | P1~P5 | P1~P5 |
| | Cell number/Vial | 2~3 × 10$^6$/vial | 2~3 × 10$^6$/vial | 2~3 × 10$^6$/vial | 2~3 × 10$^6$/vial |
| MCB~WCB | Culture medium | DMEM | DMEM | X | X |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) | | |
| | Cell culture density | 4000~5700 cells/cm$^2$ | 4000~5700 cells/cm$^2$ | | |
| | Subculturing period | 3~4 days | 3~4 days | | |
| | Medium change | X | X | | |
| | Subculture (Passage) | P6~P9 | P6~P9 | | |
| Final product | Culture medium | DMEM | DMEM | α-MEM | α-MEM |
| | Antibiotic (concentration) | Penicillin-streptomycin Penicillin (100 units/mL) Streptomycin (100 μg/mL) | Penicillin-streptomycin Penicillin (100 units/mL) Streptomycin (100 μg/mL) | Gentamicin 20 μg/mL | Gentamicin 20 μg/mL |
| | Cell culture density | 4000~5700 cells/cm$^2$ | 4000~5700 cells/cm$^2$ | 700~1000 cells/cm$^2$ | 700~1000 cells/cm$^2$ |
| | Subculturing period | 3~4 days | 3~4 days | 5~7 days | 5~7 days |
| | Medium change | X | X | ○ (every 3~4 days) | ○ (every 3~4 days) |
| | Subculture (Passage) | P10~P12 | P10~P12 | P6~P8 | P6~P8 |
| | Final vol. per Bag (Body weight) | — | 7.5 mL (25 Kg) | 6 mL (20 Kg) | 6 mL (20 Kg), 12 mL (40 Kg) |

TABLE 5

| Process | Items | Fresh Product | Process A | Process B-3 (Frozen Product) |
|---|---|---|---|---|
| Bone marrow~MCB | Culture medium Antibiotic (concentration) | DMEM Penicillin-streptomycin | DMEM Penicillin-streptomycin | α-MEM Gentamicin |

TABLE 5-continued

| Process | Items | Fresh Product | Frozen Product Process A | Process B Process B-3 |
|---|---|---|---|---|
| | | Penicillin (100 units/mL) Streptomycin (100 µg/mL) | Penicillin (100 units/mL) Streptomycin (100 µg/mL) | 20 µg/mL |
| | Cell culture density | 4000~5700 cells/cm² | 4000~5700 cells/cm² | 50~1000 cells/cm² |
| | Subculturing period | 3~4 days | 3~4 days | 5~14 days |
| | Medium change | X | X | ○ (every 3~4 days) |
| | Subculture (Passage) | P1~P5 | P1~P5 | P1~P5 |
| | Cell number/Vial | 2~3 × 10⁶/vial | 2~3 × 10⁶/vial | 2~3 × 10⁶/vial |
| MCB~ WCB | Culture medium | DMEM | DMEM | X |
| | Antibiotic (concentration) | Penicillin-streptomycin Penicillin (100 units/mL) Streptomycin (100 µg/mL) | Penicillin-streptomycin Penicillin (100 units/mL) Streptomycin (100 µg/mL) | |
| | Cell culture density | 4000~5700 cells/cm² | 4000~5700 cells/cm² | |
| | Subculturing period | 3~4 days | 3~4 days | |
| | Medium change | X | X | |
| | Subculture (Passage) | P6~P9 | P6~P9 | |
| Final Product | Culture medium | DMEM | DMEM | α-MEM |
| | Antibiotic (concentration) | Penicillin-streptomycin Penicillin (100 units/mL) Streptomycin (100 µg/mL) | Penicillin-streptomycin Penicillin (100 units/mL) Streptomycin (100 µg/mL) | Gentamicin 20 µg/mL |
| | Cell culture density | 4000~5700 cells/cm² | 4000~5700 cells/cm² | 700~1000 cells/cm² |
| | Subculturing period | 3~4 days | 3~4 days | 5~7 days |
| | Medium change | X | X | ○ (every 3~4 days) |
| | Subculture (Passage) | P10~P12 | P10~P12 | P6~P8 |
| | Final vol. per Bag (Body weight) | — | 7.5 mL (25 Kg) | 6 mL (20 Kg), 12 mL (40 Kg) |

More specifically, the subfractionation culture process and proliferation culture of the bone marrow-derived mesenchymal stem cells of the present disclosure were performed as follows.

The hip of a bone marrow donor was anesthetized with local anesthetics. Then, the bone marrow was collected by piercing the needle into the hip bone. 14 ml Dulbecco's modified Eagle's medium (DMEM, GIBCO-BRL, Life-technologies, MD, USA) containing 20% FBS and 1% penicillin/streptomycin, and 1 ml human bone marrow were placed in a 100 mm culture vessel, and the mixture was cultured in a 5% $CO_2$ cell incubator at 37° C. for 2 hours. After the culture, the culture vessel was slightly tilted to one side, and only the supernatant of the culture vessel was transferred to a new vessel while the cells attached to the bottom were prevented from falling down.

The same procedure was repeated one more time, and the resulting culture solution was transferred to a culture vessel (Becton Dickinson) coated with collagen on the bottom thereof and cultured at 37° C. for 2 hours. The culture solution was transferred to a new vessel coated with collagen. After 24 hours, the culture solution was transferred to the new container. Again, after 24 hours, the culture solution was transferred to a new vessel. Finally, after 48 hours, the culture solution was transferred to a new vessel. Then, it was visually confirmed that remaining cells were grown and adhered to the bottom of the culture vessel. It can be assumed that cells which can come up to this step through the subfractionation culture process have much smaller than other cells. After about 10 days to about 14 days, the cells formed a single colony. These monoclonal cell groups were treated with trypsin to be isolated. Then, the cells were transferred to a 6-well culture vessel at 50-200 cells/cm². The cells were cultured in a 5% $CO_2$ cell incubator at 37° C. for 4 to 5 days. Then, when the cells were grown to about 80%, the cells were treated with 0.25% trypsin/1 mM EDTA (GIBCO-BRL), thereby obtaining the cells. Then, the cells were transferred to 75 cm² culture vessel and subcultured.

When the cells were cultured at a cell density which was reduced to 1000 cells/cm² in the early passage 2 to passage 5 but other procedures were regulated in the same manner, the proliferation ability and stem cell characteristics of MSCs were excellently maintained to induce efficient proliferation even in the same passage. In particular, when the cells were cultured at a cell density lowered as described above, it can exclude a process of preparing a working cell bank (WCB) in MSCs, which is required in the conventional process, thereby shortening the cell production period efficiently. In particular, when the passage is reduced, cells with less aging can be obtained in a large amount. It is expected that such cells are used as a therapeutic agent to lead to excellent therapeutic effect.

Further, when α-MEM supplemented with an antioxidant is used as a culture medium, the antioxidant treatment can effectively reduce the ROS stress induced in high density cell culture and restore the cell proliferation ability of MSCs, thereby shortening the cell passage significantly and rapidly and stably obtaining single colony MSCs in a fresh state without aging, which maintains the characteristics of MSCs.

In summary, the low density cell culture may not only obtain a large number of cells in the short term, thereby simplifying the production process, but also obtain cells with non-aging to maintain the intact characteristics of MSCs in the long-term culture. Therefore, this leads to high quality stem cell production. Accordingly, it is expected that these are highly useful for large-scale production technology for cell therapeutic agent development.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A subfractionation culturing method of a stem cell and proliferation thereof, the method comprising the steps of:
   1) culturing bone marrow isolated from an individual;
   2) transferring a supernatant of step 1) to a new culture vessel;
   3) culturing the supernatant of step 2);
   4) transferring the supernatant of step 3) to a new culture vessel;
   5) culturing the resultant supernatant at 370 C for 1-3 hours;
   6) transferring the resultant supernatant to a new culture vessel;
   7) culturing the resultant supernatant for 12-36 hours;
   8) repeating steps 6) and 7) two or three times;
   9) transferring the supernatant of step 8) to a new culture vessel;
   10) culturing the supernatant of step 9) at 370 C for 24-72 hours;
   11) isolating a monoclonal stem cell colony from the supernatant of step 10);
   12) obtaining monoclonal stem cells of the monoclonal stem cell colony of step 11);
   13) seeding and subculturing the monoclonal stem cells of step 12) in a new culture vessel at a seeding density of 50-1000 cells/cm$^2$ in a culture for passage one;
   14) subculturing the monoclonal stem cells of step 13) for 2, 3, and 5 passages, wherein the monoclonal stem cells from previous passages are reseeded in a new culture vessel at a cell density of 700-1000 cells/cm$^2$ for 2, 3, and 5 passages; and
   15) obtaining the monoclonal stem cells from step 14), wherein a proliferation rate of the monoclonal stem cells obtained in step 15) is at least 3.08 to at most 48.5 times of a proliferation rate of comparative monoclonal stem cells obtained in the same method except for that the seeding density of 50-1000 cells/cm$^2$ in step 13) and the cell density of 700-1000 cells/cm$^2$ in step 14) are replaced with a cell density of 4000 cells/cm$^2$.

2. The method of claim 1, wherein the seeding density of step 13) and step 14) is 100 cells/cm$^2$.

3. The method of claim 1, wherein the culture vessel of step 13) and step 14) is supplemented with an antioxidant.

4. The method of claim 3, wherein the antioxidant is present at a concentration of 10-30 µg/ml.

5. The method of claim 1, wherein the culture vessel of step 13) and step 14) is Dulbecco's Minimal Essential Medium (DMEM) or α-Minimal Essential Medium (α-MEM).

6. The method of claim 1, wherein the culture vessel of step 13) and step 14) is supplemented with gentamycin.

7. The method of claim 1, wherein the stem cell obtained by the method has an osteocyte differentiation ability the monoclonal stem cells are capable of osteogenic lineage differentiation.

8. The method of claim 1, wherein the method does not comprise a process of preparing a working cell bank.

* * * * *